US006251871B1

(12) United States Patent
Jin et al.

(10) Patent No.: US 6,251,871 B1
(45) Date of Patent: *Jun. 26, 2001

(54) P16 EXPRESSION CONSTRUCTS AND THEIR APPLICATION IN CANCER THERAPY

(75) Inventors: Xiaomei Jin; Jack A. Roth, both of Houston, TX (US)

(73) Assignee: Board of Regents, The University of Texas System, Austin, TX (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/910,722

(22) Filed: Aug. 13, 1997

Related U.S. Application Data

(63) Continuation of application No. 08/502,881, filed on Jul. 17, 1995.

(51) Int. Cl.[7] .......................... A61K 48/00; C12N 15/86; C07H 21/04
(52) U.S. Cl. ...................... 514/44; 435/320.1; 536/23.5
(58) Field of Search .................................. 536/23.1, 23.5; 435/320.1; 514/44; 424/93.1, 93.21

(56) References Cited

U.S. PATENT DOCUMENTS

| | | | |
|---|---|---|---|
| 5,399,346 | 3/1995 | Anderson et al. | 424/93.21 |
| 5,624,819 | 4/1997 | Skolnick et al. | 435/69.1 |
| 5,672,508 | 9/1997 | Gyuris et al. | 435/320.1 |
| 5,691,198 | 11/1997 | Jin et al. | 435/320.1 |
| 5,739,027 | 4/1998 | Kamb | 435/240.2 |
| 5,747,469 | 5/1998 | Roth et al. | 514/44 |
| 5,801,236 | 9/1998 | Kamb | 536/24.31 |

FOREIGN PATENT DOCUMENTS

| | | |
|---|---|---|
| 0273085 | 7/1988 | (EP) . |
| WO 94/09135 | 4/1994 | (WO) . |
| WO9428152 | 12/1994 | (WO) . |
| WO 95/25429 | 9/1995 | (WO) . |
| WO 95/25813 | 9/1995 | (WO) . |
| WO 95/28169 | 10/1995 | (WO) . |
| WO 95/28483 | 10/1995 | (WO) . |
| WO 95/30002 | 11/1995 | (WO) . |
| WO 96/25507 | 8/1996 | (WO) . |
| WO 98/35554 | 8/1998 | (WO) . |

OTHER PUBLICATIONS

Arap et al., "Replacement of the p16/CDKN2 Gene Suppresses Human Glioma Cell Growth," *Cancer Research*, 55:1351–1354, Mar., 1995.

Baichwal and Sugden, "Vectors For Gene Transfer Derived From Animal DNA Viruses: Transient and Stable Expression of Transferred Genes," In: *Gene Transfer,* R. Kucherlapati, ed., New York, Plenum Press, pp. 117–148, 1986.

Benvenisty and Reshef, "Direct Introduction of Genes Into Rats and Expression of the Genes," *Proc. Natl. Acad. Sci. USA,* 83:9551–9555, Dec., 1986.

Boshart et al., "A Very Strong Enhancer Is Located Upstream of an Immediate Early Gene of Human Cytomegalovirus," *Cell,* 41:521–530, 1985.

Caldas et al., "Frequent somatic mutations and homozygous deletions of the p16 (MTS1) gene in pancreatic adenocarcinoma," *Nature Genetics,* 8:27–32, Sep., 1994.

Chang et al., "Foreign Gene Delivery and Expression in Hepatocytes Using a Hepatitis B Virus Vector," *Hepatology* (Abstract), 42nd Annual Meeting of The American Association for the Study of Liver Diseases, Chicago, Illinois, 14(4)(Pt. 2):124A, Abstract No. 307, Nov., 1991.

Cheng et al., "p16 Alterations and Deletion Mapping of 9p21–9p22 in Malignant Mesothelioma," *Cancer Research,* 54:5547–5551, Nov., 1994.

Culver et al., "In Vivo Gene Transfer with Retroviral Vector–Producer Cells for Treatment of Experimental Brain Tumors," *Science,* 256:1550–1552, Jun., 1992.

Dubensky et al., "Direct transfection of viral and plasmid DNA into the liver or spleen of mice," *Proc. Natl. Acad. Sci. USA,* 81:7529–7533, Dec., 1984.

Fearon et al., "Identification of a Chromosome 18q Gene That Is Altered in Colorectal Cancers," *Science,* 247:49–56, Jan., 1990.

Friedmann, "Progress Toward Human Gene Therapy," *Science,* 244:1275–1281, Jun., 1989.

Fujiwara et al., "Therapeutic Effect of a Retroviral WildType p53 Expression Vector in an Orthotopic Lung Cancer Model," *Journal of the National Cancer Institute,* 86(19):1458–1462, Oct., 1994.

Ghosh and Bachhawat, "Targeting of Liposomes to Hepatocytes," In: *Liver Diseases, Targeted Diagnosis and Therapy Using Specific Receptors and Ligands,* G. Wu, C. Wu, eds., New York: Marcel Dekker, pp. 87–103, 1991.

Graham and Prevec, "Adenovirus–Based Expression Vectors and Recombinant Vaccines," *Biotechnology,* 20:363–390, 1992.

Graham and Prevec, "Manipulation of Adenovirus Vectors," In: *Methods in Molecular Biology: Gene Transfer and Expression Protocols,* E.J. Murray (ed.), Clifton, NJ: Humana Press, 7:109–128, 1991.

Gruis et al., "Genetic Evidence in Melanoma and Bladder Cancers that p16 and p53 Function in Separate Pathways of Tumor Suppression," *American Journal of Pathology,* 146(5):1199–1206, May, 1995.

(List continued on next page.)

Primary Examiner—Deborah J. Clark
(74) Attorney, Agent, or Firm—Fulbright & Jaworski

(57) ABSTRACT

A variety of genetic constructs are disclosed that will find both in vitro and in vivo use in the area of tumor biology and cancer therapy. In particular, expression constructs are provided that contain a p16 encoding region and other regulatory elements necessary for the expression of a p16 transcript. One version of the expression construct is a replication-deficient adenoviral vector. Also provided are methods for the transformation of cell lines and the inhibition of cancer cell proliferation.

13 Claims, 5 Drawing Sheets

OTHER PUBLICATIONS

Grunhaus and Horwitz, "Adenoviruses as cloning vectors," *Virology*, 3:237–252, 1992.

Grunicke and Maly, "Role of GTPases and GTPase Regulatory Proteins in Oncogenesis," *Critical Reviews in Oncogenesis*, 4(4):389–402, 1993.

Harbour et al., "Abnormalities in Structure and Expression of the Human Retinoblastoma Gene in SCLC," *Science*, 241:353–357, Jul., 1988.

Herman et al., "Abnormal DNA methylation frequently inactivates the putative tumor suppressor CKDN2/p16 in many tumor types," Abstract No. 1201, Proceedings of The American Association for Cancer Research, 36:201, Mar., 1995.

Herz and Gerard, "Adenovirus–mediated transfer of low density lipoprotein receptor gene acutely accelerates cholesterol clearance in normal mice," *Proc. Natl. Acad. Sci. USA*, 90:2812–2816, Apr., 1993.

Hesdorffer et al., "Efficient Gene Transfer in Live Mice Using a Unique Retroviral Packaging Line," *DNA and Cell Biology*, 9(10):717–723, 1990.

Hussussian et al., "Germline p16 mutations in familial melanoma," *Nature Genetics*, 8:15–21, Sep., 1994.

Kamb et al., A Cell Cycle Regulator Potentially Involved.

Kamb et al., "Analysis of the p16 gene (CDKN2) as a candidate for the chromosome 9p melanoma susceptibility locus," *Nature Genetics*, 8:22–26, Sep., 1994.

Kamb et al., "Rates of p16 (MTS1) Mutations in Primary Tumors with 9p Loss," *Science*, 265:415–417, Jul., 1994.

Kaneda et al., "Increased Expression of DNA Cointroduced with Nuclear Protein in Adult Rat Liver," *Science*, 243:375–378, Jan., 1989.

Le Gal La Salle et al., "An Adenovirus Vector for Gene Transfer into Neurons and Glia in the Brain," *Science*, 259:988–990, Feb., 1993.

Levrero et al., "Defective and nondefective adenovirus vectors for expressing foreign genes in vitro and in vivo," *Gene*, 101:195–202, 1991.

Li et al., "Assessment of Recombinant Adenoviral Vectors for Hepatic Gene Therapy," *Human Gene Therapy*, 4:403–409, 1993.

Markowitz et al., "A Safe Packaging Line for Gene Transfer: Separating Viral Genes on Two Different Plasmids," *Journal of Virology*, 62(4):1120–1124, Apr., 1988.

Marx, "Learning How to Suppress Cancer," *Science*, 261:1385–1387, Sep., 1993.

Mitsudomi et al., "p53 gene mutations in non–small–cell lung cancer cell lines and their correlation with the presence of ras mutations and clinical features," *Oncogene*, 7:171–180, 1992.

Mori et al., "Frequent Somatic Mutation of the MTS1/CDK4I (Multiple Tumor Suppressor/Cyclin–dependent Kinase 4 Inhibitor) Gene in Esophageal Squamous Cell Carcinoma," *Cancer Research*, 54:3396–3397, Jul., 1994.

Mulligan, "The Basic Science of Gene Therapy," *Science*, 260:926–932, May., 1993.

Nicolau et al., "Liposomes as Carriers for in Vivo Gene Transfer and Expression," *Methods in Enzymology*, 149:157–176, 1987.

Nobori et al., "Deletions of the cyclin–dependent kinase–4 inhibitor gene in multiple human cancers," *Nature*, 368:753–756, Apr., 1994.

Okamoto et al., "Mutations and altered expression of $p16^{INK4}$ in human cancer," *Proc. Natl. Acad. Sci. USA*, 91:11045–11049, Nov., 1994.

Okamoto et al., "Mutations in the $p16^{INK4}$/MTS1/CDKN2, $p15^{INK4B}$/MTS2, and p18 Genes in Primary and Metastatic Lung Cancer," *Cancer Research*, 55:1448–1451, Apr., 1995.

Orlow et al., "Chromosome 9 Allelic Losses and Microsatellite Alterations in Human Bladder Tumors," *Cancer Research*, 54:2848–2851, Jun., 1994.

Ragot et al., "Efficient adenovirus–mediated transfer of a human minidystrophin gene to skeletal muscle of mdx mice," *Nature*, 361:647–650, Feb., 1993.

Renan, "Cancer genes: current status, future prospects, and applications in radiotherapy/oncology," *Radiotherapy and Oncology*, 19:197–218, 1990.

Rich et al., "Development and Analysis of Recombinant Adenoviruses for Gene Therapy of Cystic Fibrosis," *Human Gene Therapy*, 4:461–476, 1993.

Ridgway, "Mammalian Expression Vectors," In: *Vectors: A Survey of Molecular Cloning Vectors and Their Uses*, R.L. Rodriguez, D.T. Denhardt, eds., Stoneham: Butterworth, pp. 467–492, 1988.

Rosenfeld et al., "In Vivo Transfer of the Human Cystic Fibrosis Transmembrane Conductance Regulator Gene to the Airway Epithelium," *Cell*, 68:143–155, Jan., 1992.

Serrano et al., "A new regulatory motif in cell–cycle control causing specific inhibition of cyclin D/CDK4," *Nature*, 366:704–707, Dec., 1993.

Serrano et al., "Inhibition of Ras–Induced Proliferation and Cellular Transformation by $p16^{INK4}$," *Science*, 267:249–252, Jan., 1995.

Stratford–Perricaudet and Perricaudet, "Gene transfer into animals: the promise of adenovirus," *Human Gene Transfer*, 219:51–61, 1991.

Stratford–Perricaudet et al., "Evaluation of the Transfer and Expression in Mice of an Enzyme–Encoding Gene Using a Human Adenovirus Vector," *Human Gene Therapy*, 1:241–256, 1990.

Takahashi et al., "p53: A Frequent Target for Genetic Abnormalities in Lung Cancer," *Science*, 246:491–494, Oct., 1989.

Wagner et al., "Antisense Gene Inhibition by Oligonucleotides Containing C–5 Propyne Pyrimidines," *Science*, 260:1510–1513, Jun., 1993.

Zhang et al., "Generation and Identification of Recombinant Adenovirus by Liposome–Mediated Transfection and PCR Analysis," *BioTechniques*, 15(5):868–873, 1993.

Zhang et al., High–efficiency gene transfer and high–level expression of wild–type p53 in human lung cancer cells mediated by recombinant adenovirus, *Cancer Gene Therapy*, 1(1):5–13, 1994.

Jin et al., "Cell cycle arrest and inhibition of tumor cell proliferation by the $p16^{INK4}$ gene mediated by an adenovirus vector," *Canc. Res.*, 55(15):3250–3253 (Aug. 1, 1995).

Marx, "New tumor suppressor may rival p53," *Science*, 264:344–345, 1994.

Gura et al., *Science*, 270:575–577, 1995.

Miller et al., *FASEB J*, 9:190–199, 1995.

Zhang et al., *J Cell Biochem*, 248:02511, 1994.

Culver et al., *TIG*, 10(5):174–178, 1994.

Hodgson, *Exp Opin Ther Pat*, 5(5):459–468, 1995.

Verma et al. Gene therapy—Promises, problems and prospects. Nature, vol. 389, pp. 239–242, Sep. 18, 1997.*

Orkin et al. Report and Recommendations of the Panel to Assess the NIH Investment in Research on Gene Therapy. Distributed by the National Institutes of Health, Bethesda, MD, or obtanable @www.nih.gov., Dec. 7, 1995.*

Marshall, E. Gene Therapy's Growing Pains. Science, vol. 269, pp. 1050–1055, Aug. 25, 1995.*

Wills, et al. Development and Characterization of Recombinant Adenoviruses Encoding Human p53 for Gene Therapy of Cancer. Human Gene Therapy, vol. 5, pp. 1079–1088, Sep. 1994.*

* cited by examiner

```
  1 cggagaggg gagaacagac aacgggcggc ggggagcagc atggagccgg cggcggggag
 61 cagcatggag ccttcggctg actggctggc cacggccgcg gcccggggtc gggtagagga
121 ggtgcgggcg ctgctggagg cggggcgct  cgggggcgct gcccaacgca ccgaatagtt acggtcggag
181 gccgatccag gtcatgatga gtcatgatga tgggcagcgc ccgagtggcg gagctgctgc tgctccacgg
241 cgcggagccc aactgcgccg accccgccac tctcacccga cccgtgcacg acgctgcccg
301 ggaggcttc  ctggacacgc tggtggtgct gcaccgggcc ggggcgcggc tggacgtgcg
361 cgatgcctgg ggccgtctgc ccgtggacct ggctgaggag ctgggccatc gcgatgtcgc
421 acggtacctg cgcgcggctg cgggggcac  cagaggcagt aaccatgccc gcatagatgc
481 cgcggaagt  ccctcagaca tccccgattg aaagaaccag agaggctctg agaaccctcg
541 ggaaacttag atcatcagtc accgaaggtc ctacagggcc acaactgccc ccgccacaac
601 ccacccccgct ttcgtagttt tcatttagaa aatagagctt ttaaaaatgt cctgcctttt
661 aacgtagata taagccttcc cccactaccg taaatgtcca tttatatcat tttttatata
721 ttcttataaa aatgtaaaaa agaaaaacac cgcttctgcc ttttcactgt gttggagttt
781 tctggagtga gcactcacgc cctaagcgca cattcatgtg ggcatttctt gcgagcctcg
841 cagcctccgg aagctgtcga cttcatgaca agcattttgt gaactaggga agctcagggg
901 ggttactggc ttctcttgag tcacactgct agcaaatggc agaaccaaag ctcaaataaa
961 aataaaataa ttttcattca ttcactc
```

FIG. 1A

```
  1  MEPAAGSSME  PSADWLATAA  ARGRVEEVRA  LLEAGALPNA  PNSYGRRPIQ   50
 51  VMMMGSARVA  ELLLLHGAEP  NCADPATLTR  PVHDAAREGF  LDTLVVLHRA  100
101  GARLDVRDAW  GRLPVDLAEE  LGHRDVARYL  RAAAGGTRGS  NHARIDAAEG  150
151  PSDIPD                                                     156
```

FIG. 1B

P16 EXPRESSION CONSTRUCTS AND THEIR APPLICATION IN CANCER THERAPY

This is a continuation of application Ser. No. 08/502,881 filed Jul. 17, 1995.

The government may own certain rights in the present invention pursuant to grant number CA 45187 from the National Institutes of Health and Core Grant CA 16672.

BACKGROUND OF THE INVENTION

1. Field of the Invention

The present invention relates generally to the field of tumor biology. In particular, the invention relates to a nucleic acid encoding a tumor suppressor and its use in inhibiting tumor growth. In one embodiment, the invention relates to expression constructs encoding p16 and their use in inhibiting cancer.

2. Description of the Related Art

Cancer is one of the leading causes of human disease, being responsible for 526,000 deaths in the United States each year (Boring et al., 1993). Lung cancer alone kills more than 140,000 people annually in the United States. Recently, age-adjusted mortality from lung cancer has surpassed that from breast cancer in women. Although implementation of smoking-reduction programs has decreased the prevalence of smoking, lung cancer mortality rates will remain high well into the twenty-first century. Unfortunately, current treatment methods for cancer, including radiation therapy, surgery and chemotherapy, are known to have limited effectiveness. The rational development of new therapies for lung cancer largely will depend on gaining an improved understanding of the biology of cancer at the molecular level.

With advances in molecular genetics and biology, it has become evident that altered expression of normal genes can lead to the initiation of transforming events that result in the creation of cancer cells. The conventional therapy for malignancy, such as chemotherapy and radiation, has focused on mass cell killing without specific targeting, often resulting in damaging side effects. A new direction in cancer therapy is to deliver a normal gene to replace or correct the mutated gene, thereby altering the malignant phenotype of transformed cells. Several expression constructs have been developed in order to deliver a gene into somatic cells with high efficiency.

Cells are regulated in both positive (stimulatory) and negative (suppressive) manners. Loss of negative regulation of cell growth is often found in malignant cells. Accumulating molecular genetic evidence has revealed that loss of negative regulators, or increase in positive regulators in normal cells, can produce such cellular growth abnormalities. Most negative regulators (Marx, 1993; Grunicke and Maly, 1993), referred to as tumor suppressors, have been found to be involved either in direct control of the cell cycle (e.g., Rb, p53, WT-1) or in the signaling pathway leading to cell growth and differentiation (e.g., NF-1). In addition, recent data suggest that genes related to the maintenance of cell architecture and polarity also may function as tumor suppressors (Marx, 1993; Fearon et al., 1990; Trofatter et al., 1993).

The major transitions of the eukaryotic cell cycle are triggered by cyclin-dependent kinases, or CDK's. One CDK, cyclin-dependent kinase 4 (CDK4), regulates progression through the $G_1$. The activity of this enzyme may be to phosphorylate Rb at late $G_1$. The activity of CDK4 is controlled by an activating subunit, D-type cyclin, and by an inhibitory subunit, the $p16^{INK4}$ protein. $p16^{INK4}$ has been biochemically characterized as a protein that specifically binds to and inhibits CDK4, and thus may regulate Rb phosphorylation (Serrano et al., 1993; Serrano et al., 1995). Since the $p16^{INK4}$ protein is a CDK4 inhibitor (Serrano, 1993), deletion of this gene may increase the activity of CDK4, resulting in hyperphosphorylation of the Rb protein. p16 also is known to regulate the function of CDK6.

$p16^{INK4}$ belongs to a newly described class of CDK-inhibitory proteins that also includes $p15^B$, $p21^{WAF1}$, and $p27^{KIP1}$. The $p16^{INK4}$ gene maps to 9p21, a chromosome region frequently deleted in many tumor types. Homozygous deletions and mutations of the $p16^{INK4}$ gene are frequent in human tumor cell lines. This evidence suggests that the $p16^{INK4}$ gene is a tumor suppressor gene. This interpretation has been challenged, however, by the observation that the frequency of the $p16^{INK4}$ gene alterations is much lower in primary uncultured tumors than in cultured cell lines (Caldas et al., 1994; Cheng et al., 1994; Hussussian et al., 1994; Kamb et al., 1994; Kamb et al., 1994; Mori et al., 1994; Okamoto et al., 1994; Nobori et al., 1995; Orlow et al., 1994; Arap et al., 1995). Restoration of wild-type $p16^{INK4}$ function by transfection with a plasmid expression vector reduced colony formation by some human cancer cell lines (Okamoto, 1994; Arap, 1995).

SUMMARY OF THE INVENTION

The present invention addresses the need for improved therapy for lung and other p16-associated cancers by providing expression constructs containing a nucleic acid encoding p16. It also is an object of the present invention to provide methods for the use of such compositions and, in particular, use in the treatment of cancer. In another embodiment, the present invention encompasses methods for transforming cells using a p16 nucleic acid in an expression construct.

The present invention also encompasses expression constructs that comprise a promoter functional in eukaryotic cells and a nucleic acid encoding p16, the nucleic acid being under transcriptional control of the promoter.

In a preferred embodiment, the expression constructs further comprise a polyadenylation signal. In another embodiment, the constructs further comprise a selectable marker. In a further embodiment, the expression construct is an adenovirus. In a preferred embodiment, the expression construct is an adenovirus that lacks at least a portion of the E1 region.

In certain embodiments, the nucleic acid is a cDNA. In other embodiments the nucleic acid is a genomic DNA. Still other embodiments include a combination of cDNA and genomic DNA, for example, in a mini-gene construct. In an exemplary embodiment the nucleic acid is positioned in a sense orientation with respect to said promoter. In another embodiment the nucleic acid is positioned in an antisense orientation.

The present invention also includes pharmaceutical compositions comprising an expression construct with a promoter functional in eukaryotic cells and a nucleic acid encoding p16, along with a pharmaceutically acceptable buffer, solvent or diluent. In certain embodiments, the expression construct and pharmaceutically acceptable buffer, solvent or diluent are supplied in a kit.

The invention also provides a method for restoring proper p16 function in a cell that lacks p16 function or expresses a functional p16 that is improperly compartmentalized. This method comprises contacting such a cell with an expression construct as described above, wherein the nucleic acid is positioned in a sense orientation. In an exemplary embodiment of the invention, the cell is a transformed cell and the contacting reverses the transformed phenotype. In a further embodiment, the cell is a lung, bladder, leukemia or melanoma cancer cell and, in still a further embodiment, the expression construct is an adenovirus.

The present invention further comprises a method for inhibiting p16 function in a cell. This method comprises contacting such a cell with an expression construct as described above, wherein the nucleic acid is positioned in an antisense orientation. In a further embodiment, the expression construct is an adenovirus.

Another embodiment of the invention is a method of treating a mammal with cancer. This method comprises administering to an animal a pharmaceutical composition comprising an expression construct having a promoter functional in eukaryotic cells and a nucleic acid encoding p16, positioned in a sense orientation, in a pharmaceutically acceptable buffer, solvent or diluent. In a particular embodiment of the invention, the mammal is a human. In another embodiment, administering is via intravenous injection. In a further embodiment, the cancer is lung cancer.

In further embodiments the present invention encompasses methods for detecting cancer cells in a sample by detecting p16 or a nucleic acid encoding a p16.

BRIEF DESCRIPTION OF THE DRAWINGS

FIG. 1A—Nucleotide Sequence of p16. (SEQ ID NO:1)

FIG. 1B—Amino Acid Sequence of p16. (SEQ ID NO:2)

DETAILED DESCRIPTION OF THE PREFERRED EMBODIMENTS

Figure 2:
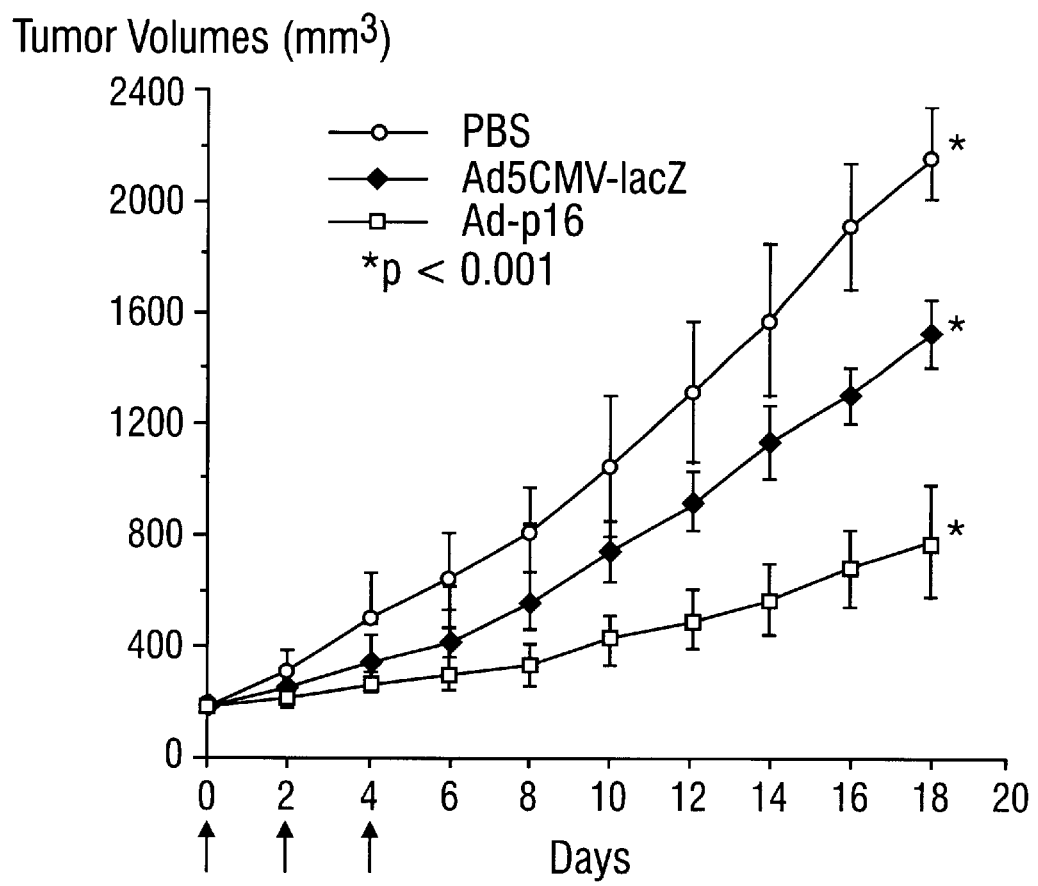
FIG. 2—Cell growth curves of the Ad-p16 infected cell lines. Cells were inoculated at densities of $5 \times 10^4$ in 60 mm culture dishes 24 h before infection and infected with Ad-p16 or Ad5CMV-lacZ at 50 PFU/cell. Culture medium alone was used for mock infection. Triplet cultures of each cell line for each treatment were counted daily from postinfection day 1 to day 6. The curves are plotted from a representative assay of three experiments (Mean±SD).
Figure 3A:
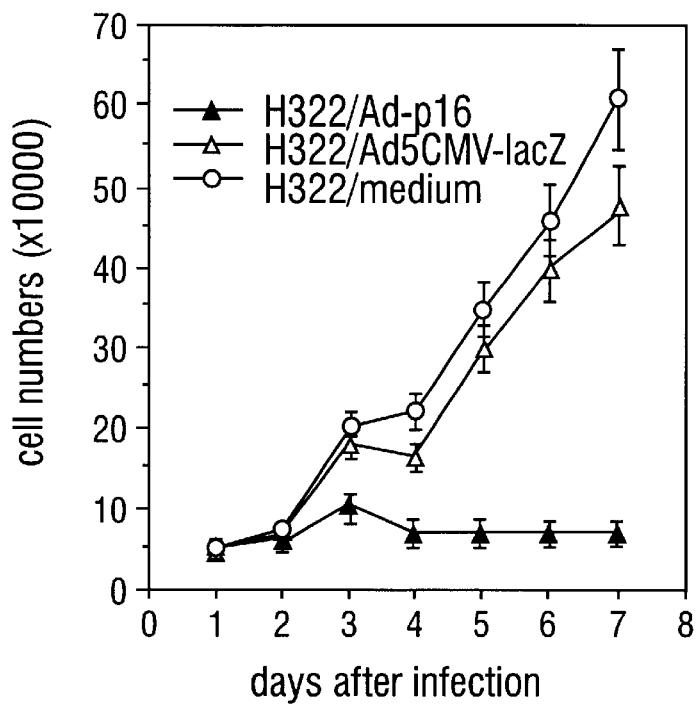
FIG. 3—Tumor growth in mice following intratumoral injections of Ad-p16, control virus AD5CMV-lacZ or PBS (5 mice per group). Subcutaneous tumor nodules were created by injecting $5 \times 10^6$ H460 cells suspended in 0.1 ml of PBS into the dorsal flanks of nude mice. Tumor nodules (180 to 220 mm$^3$) were treated 16 days after cell implantation. Direct intratumoral injection of Ad-p16, Ad5CMV-lacZ, or PBS was performed. For each tumor nodule, $10^{10}$ PFU of Ad-p16 or Ad5CMV-lacZ divided equally in three doses was injected on alternate days for 6 days. PBS injection served as a control. Tumor size was measured with linear calipers in two orthogonal directions on alternate days after injection and tumor volumes were calculated (Mean±SD).
Figure 3B:
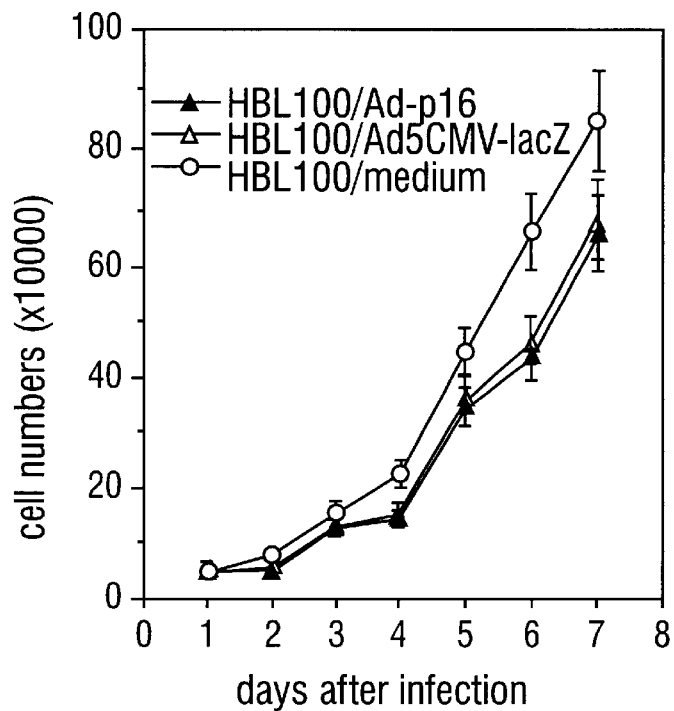
Figure 3C:
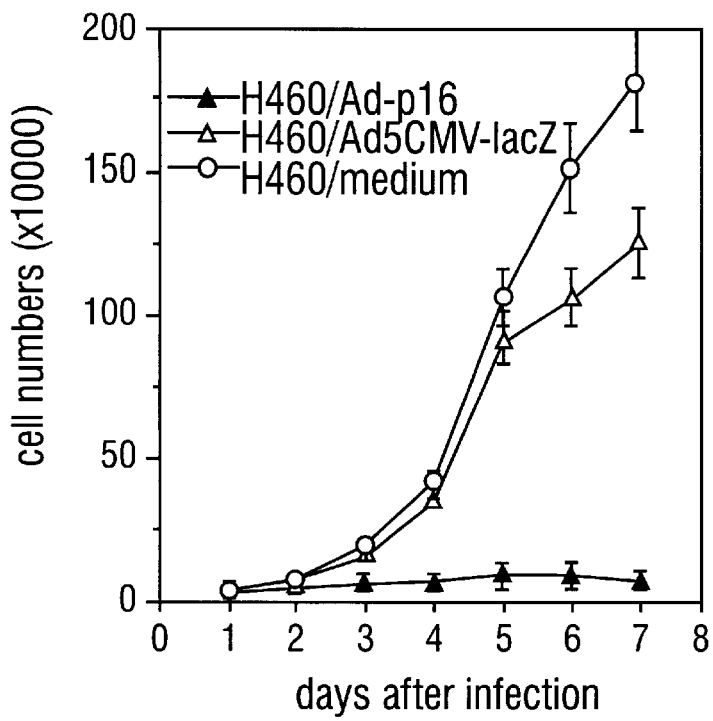
Figure 3D:
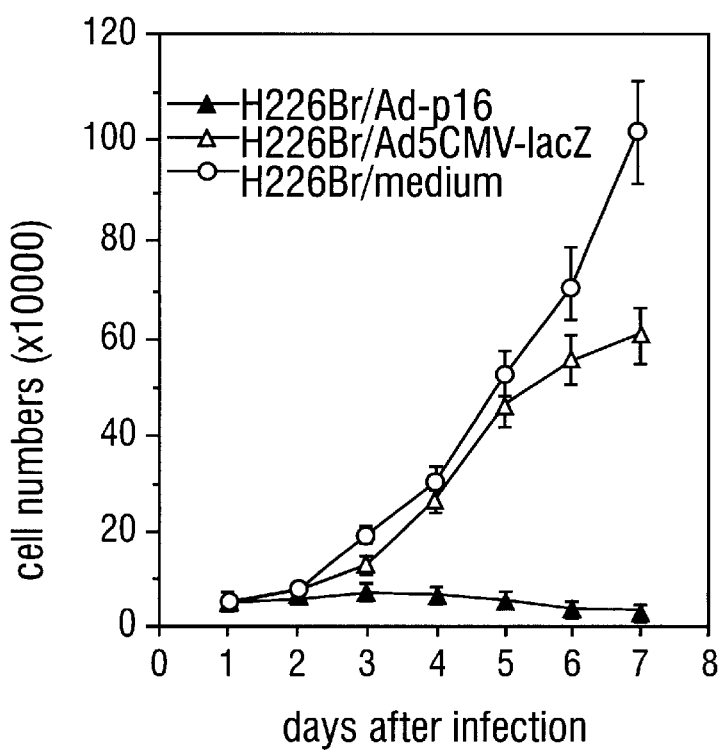

Evidence now has accumulated that dysregulation of certain genes involved in control of the cell cycle contributes to the malignant progression of cells. For example, premature entry of a cell into the next phase of the cell cycle may result in incomplete repair of DNA damage and subsequent genomic instability. As mentioned above, cyclin-dependent kinases play an important role in cell cycle regulation. It is known that p16$^{INK4}$ protein can complex with cyclin D1-CDK4 and inhibit its interaction with Rb, thus retarding passage through the cell cycle. The presence of point mutations and homozygous deletions in a high percentage of cancer cell lines further suggests that p16$^{INK4}$ may function as a tumor suppressor gene.

Mutations in primary human esophageal and pancreatic cancers, bladder cancers, melanoma and NSCLC metastases have been reported, although the rates of mutations in primary tumors are lower than those for cell lines (Mori et al., 1994; Okamoto et al., 1994; Okamoto et al., 1995; Zhou et al., 1994; Cairns et al., 1994; Hussussian et al., 1994; Kamb et al., 1994; Gruis et al., 1995). Deletions and mutations may not be the primary mode of p16$^{INK4}$ inactivation, however, as hypermethylation of p16$^{INK4}$ associated with transcriptional silencing is a frequent finding in lung cancer, head and neck cancer, glioma cell lines and fresh tumors without deletions or mutations (Herman et al., 1995).

The data presented here are the first to show that p16 acts as a tumor suppressor in vivo. Thus, the present invention addresses the need for improved therapy for lung cancer and other p16-associated diseases. In particular, an expression construct capable of expressing a functional p16 product can be used to inhibit tumor cell proliferation. In addition, the present invention encompasses the use of antisense methodology, directed at p16, to transform cell lines or otherwise increase the rate or extent of growth of cells. The following description provides a more detailed explanation of these and other aspects of the present invention.

There also is evidence that p16-targeted treatments will have therapeutic implications in an anti-angiogenic approach. There are many disease where a decrease in vasculature is desirable. In addition, p16-treatments also may prove beneficial with respect to hyperproliferative disorders such as restenosis.

A. p16 AND p16-RELATED NUCLEIC ACIDS

The nucleic acid according to the present invention may encode an entire p16 gene, a functional p16 protein domain, or any p16 polypeptide, peptide or fragment that is sufficient to effect inhibition of CDK4. The p16 nucleic acid may be derived from genomic DNA, i.e., cloned directly from the genome of a particular organism. In preferred embodiments, however, the nucleic acid encoding p16 would comprise complementary DNA (cDNA) or cDNA plus an intron, i.e., a mini-gene.

The term "cDNA" is intended to refer to DNA prepared using messenger RNA (mRNA) as template. The advantage of using a cDNA, as opposed to genomic DNA or DNA polymerized from a genomic, non- or partially-processed RNA template, is that the cDNA does not contain any non-coding sequences but, rather, contains only the coding region of the corresponding protein. There may be times when the full or partial genomic sequence is preferred, such as where the non-coding regions are required for optimal expression or where non-coding regions such as introns are to be targeted in an antisense strategy.

Throughout the application, the term "p16" is used synonymously with its other designations—MTS1, CDK4I and CDKN2. The use of the term "p16" also is intended to refer to all p16 homologues from other species in addition to those specified.

It also is contemplated that a given p16 may be represented by natural variants that have slightly different primary sequences but, nonetheless, are biological functional equivalents of each other (see below). In order to function according to the present invention, all that is required is that the p16 bind to CDK4. To test for such an affect, it is a simple matter to assay binding of a protein, encoded by a p16 nucleic acid, in vitro or by the use of transfection techniques as described by Serrano et al., 1993, incorporated herein by reference.

As used in this application, the term "nucleic acid encoding a p16" refers to a nucleic acid molecule that has been isolated free of total cellular nucleic acid. In preferred embodiments, the invention concerns a nucleic acid sequence essentially as set forth in FIG. 1A (SEQ ID NO:1). The term "as set forth in FIG. 1A" means that the nucleic acid sequence substantially corresponds to a portion of FIG. 1A and has relatively few codons that are not identical, or functionally equivalent, to the codons of FIG. 1A. The term "functionally equivalent codon" is used herein to refer to codons that encode the same amino acid, such as the six codons for arginine or serine, and also refers to codons that encode biologically equivalent amino acids (as in Table 1 below).

TABLE 1

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalnine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

Allowing for the degeneracy of the genetic code, sequences that have between about 50% and about 75%; or more preferably, between about 76% and about 99% of nucleotides that are identical to the nucleotides of FIG. 1A will be sequences that are "as set forth in FIG. 1A." Sequences that are essentially the same as those set forth in FIG. 1A may also be functionally defined as sequences that are capable of hybridizing to a nucleic acid segment containing the complement of FIG. 1A under standard conditions.

Suitable hybridization conditions will be well known to those of skill in the art. In certain applications, for example, substitution of amino acids by site-directed mutagenesis, it is appreciated that lower stringency conditions are required. Under these conditions, hybridization may occur even though the sequences of probe and target strand are not perfectly complementary, but are mismatched at one or more positions. Conditions may be rendered less stringent by increasing salt concentration and decreasing temperature. For example, a medium stringency condition could be provided by about 0.1 to 0.25M NaCl at temperatures of about 37° C. to about 55° C., while a low stringency condition could be provided by about 0.15M to about 0.9M salt, at temperatures ranging from about 20° C. to about 55° C. Thus, hybridization conditions can be readily manipulated, and thus will generally be a method of choice depending on the desired results.

In other embodiments, hybridization may be achieved under conditions of, for example, 50 mM Tris-HCl (pH 8.3), 75 mM KCl, 3 mM $MgCl_2$, 10 mM dithiothreitol, at temperatures between approximately 20° C. to about 37° C. Other hybridization conditions utilized could include approximately 10 mM Tris-HCl (pH 8.3), 50 mM KCl, 1.5 µM $MgCl_2$, at temperatures ranging from approximately 40° C. to about 72° C. Formamide and SDS also may be used to alter the hybridization conditions.

Naturally, the present invention also encompasses DNA segments that are complementary, or essentially complementary, to the sequence set forth in FIG. 1A. Nucleic acid sequences that are "complementary" are those that are capable of base-pairing according to the standard Watson-Crick complementary rules. As used herein, the term "complementary sequences" means nucleic acid sequences that are substantially complementary, as may be assessed by the same nucleotide comparison set forth above, or as defined as being capable of hybridizing to the nucleic acid segment of FIG. 1A under relatively stringent conditions such as those described herein. Such sequences may encode the entire p16 molecule or functional fragments thereof.

Alternatively, the hybridizing segments may be shorter oligonucleotides. Sequences of 17 bases long should occur only once in the human genome and, therefore, suffice to specify a unique target sequence. Although shorter oligomers are easier to make and increase in vivo accessibility, numerous other factors are involved in determining the specificity of hybridization. Both binding affinity and sequence specificity of an oligonucleotide to its complementary target increases with increasing length. It is contemplated that oligonucleotides of 8, 9, 10, 11, 12, 13, 14, 15, 16, 17, 18, 19, 20 or more base pairs will be used. Such oligonucleotides will find use, for example, as probes and as primers in amplification reactions.

The DNA segments of the present invention include those encoding biologically functional equivalent p16 proteins and peptides. Such sequences may arise as a consequence of codon redundancy and functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques or may be introduced randomly and screened later for the desired function.

If desired, one also may prepare fusion proteins and peptides, e.g., where the p16 coding regions are fused with coding regions for other proteins or peptides and having desired functions, such as for purification, immunodetection, stabilization or targeting purposes. Furthermore, these fusion proteins or fusion peptides might contain an intracellular targeting sequence that would direct their transport to selected cellular compartments, particularly the nucleus. These fusion proteins or fusion peptides may be expressed from a DNA construct that has been delivered to animal cells.

It also will be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to coding nucleic acid sequences that may, for example, include various non-coding sequences flanking either of the 5' or 3' portions of the coding region, such as promoters. Furthermore, affinity or detection moieties, such as digoxigenin or avidin, may be added to the nucleic acid sequences.

As mentioned above, modification and changes may be made in the primary structure of p16 (as exemplified by FIG. 1B) and still obtain a molecule having like or otherwise desirable characteristics. For example, certain amino acids may be substituted for other amino acids in a protein structure without appreciable loss of interactive binding capacity with structures such as, for example, antigen-binding regions of antibodies or binding sites on substrate molecules, receptors, or signal transduction. Since it is the interactive capacity and nature of a protein that defines that protein's biological functional activity, certain amino acid sequence substitutions can be made in a protein sequence (or, of course, its underlying DNA coding sequence) and nevertheless obtain a protein with like (agonistic) properties. Equally, the same considerations may be employed to create a protein or polypeptide with countervailing (e.g., antagonistic) properties. It is thus contemplated by the inventors that various changes may be made in the sequence of p16 proteins or peptides (or underlying DNA) without appreciable loss of their biological utility or activity.

It also is well understood by the skilled artisan that, inherent in the definition of a biologically functional equivalent protein or peptide, is the concept that there is a limit to the number of changes that may be made within a defined portion of the molecule and still result in a molecule with an acceptable level of equivalent biological activity. Biologically functional equivalent peptides are thus defined herein as those peptides in which certain, not most or all, of the amino acids may be substituted. In particular, where the N-terminus of the p16 protein is concerned, it is contemplated that only about 16 or more preferably, about 5 amino acids may be changed within a given peptide. Of course, a plurality of distinct proteins/peptides with different substitutions may easily be made and used in accordance with the invention.

Amino acid substitutions are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents.

In making changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte & Doolittle, 1982, incorporated herein by reference). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It is understood that an amino acid can be substituted for another having a similar hydrophilicity value and still obtain a biologically equivalent protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±2 is preferred, those which are within ±1 are particularly preferred, and those within ±0.5 are even more particularly preferred.

While the preceding discussion has focused on functionally equivalent polypeptides arising from amino acid changes, it will be appreciated that these changes may be effected by alteration of the encoding DNA, taking into consideration also that the genetic code is degenerate and that two or more codons may code for the same amino acid.

In addition to the peptidyl compounds described herein, the inventors also contemplate that other sterically similar compounds may be formulated to mimic the key portions of the peptide structure. Such compounds, which may be termed peptidomimetics, may be used in the same manner as the peptides of the invention and hence are also functional equivalents. The generation of a structural functional equivalent may be achieved by the techniques of modelling and chemical design known to those of skill in the art. It will be understood that all such sterically similar constructs fall within the scope of the present invention.

B. ANTISENSE CONSTRUCTS

In an alternative embodiment, the p16 nucleic acid may encode the antisense version of any of the above full-length or fragmentary nucleic acids. The sense or coding constructs will generally be used in methods for inhibiting tumor proliferation where the lack of p16 function is a problem and replacement of p16 function is desired. However, in embodiments where overexpression of p16 is a problem, such as where inhibition or suppression of p16 expression is desired, antisense molecules may be employed.

The term "antisense nucleic acid" is intended to refer to the oligonucleotides complementary to the base sequences of p16-encoding DNA or RNA. Antisense oligonucleotides, when introduced into a target cell, specifically bind to their target nucleic acid and interfere with transcription, RNA processing, transport, translation and/or stability. Targeting double-stranded (ds) DNA with oligos or oligonucleotides leads to triple-helix formation; targeting RNA will lead to double-helix formation.

Antisense constructs may be designed to bind to the promoter and other control regions, exons, introns or even exon-intron boundaries of a gene. Antisense RNA constructs, or DNA encoding such antisense RNA's, may be employed to inhibit gene transcription or translation or both within a host cell, either in vitro or in vivo, such as within a host animal, including a human subject. Nucleic acid sequences which comprise "complementary nucleotides" are those which are capable of base-pairing according to the standard Watson-Crick complementarity rules. That is, that the larger purines will base pair with the smaller pyrimidines to form combinations of guanine paired with cytosine (G:C) and adenine paired with either thymine (A:T), in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

As used herein, the terms "complementary" or "antisense sequences" mean nucleic acid sequences that are substantially complementary over their entire length and have very few base mismatches. For example, nucleic acid sequences of fifteen bases in length may be termed complementary when they have a complementary nucleotide at thirteen or fourteen positions with only a single mismatch. Naturally, nucleic acid sequences which are "completely complementary" will be nucleic acid sequences which are entirely complementary throughout their entire length and have no base mismatches.

Other sequences with lower degrees of homology also are contemplated. For example, an antisense construct which has limited regions of high homology, but also contains a non-homologous region (e.g., a ribozyme) could be designed. These molecules, though having less than 50% homology, would bind to target sequences under appropriate conditions.

While all or part of the gene sequence may be employed in the context of antisense construction, statistically, any sequence of 17 bases long should occur only once in the human genome and, therefore, suffice to specify a unique target sequence. Although shorter oligomers are easier to make and increase in vivo accessibility, numerous other factors are involved in determining the specificity of hybridization. Both binding affinity and sequence specificity of an oligonucleotide to its complementary target increases with increasing length. It is contemplated that oligonucleotides of 8, 9, 10, 11, 12, 13, 14, 15, 16, 17, 18, 19, 20 or more base pairs will be used. One can readily determine whether a given antisense nucleic acid is effective at targeting of the corresponding host cell gene simply by testing the constructs in vitro to determine whether the endogenous gene's function is affected or whether the expression of related genes having complementary sequences is affected.

In certain embodiments, one may wish to employ antisense constructs which include other elements, for example, those which include C-5 propyne pyrimidines. Oligonucleotides which contain C-5 propyne analogues of uridine and cytidine have been shown to bind RNA with high affinity and to be potent antisense inhibitors of gene expression (Wagner et al., 1993).

As an alternative to targeted antisense delivery, targeted ribozymes may be used. The term "ribozyme" is refers to an RNA-based enzyme capable of targeting and cleaving particular base sequences in p16 DNA and RNA. Ribozymes can either be targeted directly to cells, in the form of RNA oligonucleotides incorporating ribozyme sequences, or introduced into the cell as an expression construct encoding the desired ribozymal RNA. Ribozymes may be used and applied in much the same way as described for antisense nucleic acids. Ribozyme sequences also may be modified in much the same way as described for antisense nucleic acids. For example, one could incorporate non-Watson-Crick bases, or make mixed RNA/DNA oligonucleotides, or modify the phosphodiester backbone.

C. EXPRESSION CONSTRUCTS

Throughout this application, the term "expression construct" is meant to include any type of genetic construct containing a nucleic acid coding for a gene product in which part or all of the nucleic acid encoding sequence is capable of being transcribed. The transcript may be translated into a protein, but it need not be. Thus, in certain embodiments, expression includes both transcription of a p16 gene and translation of a p16 mRNA into a p16 gene product. In other embodiments, expression only includes transcription of the nucleic acid encoding a p16.

In preferred embodiments, the nucleic acid encoding a p16-derived product is under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

The particular promoter that is employed to control the expression of a nucleic acid encoding a p16 is not believed to be important, so long as it is capable of expressing the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter.

In various embodiments, the human cytomegalovirus (CMV) immediate early gene promoter, the SV40 early promoter and the Rous sarcoma virus long terminal repeat can be used to obtain high-level expression of p16. The use of other viral or mammalian cellular or bacterial phage promoters which are well-known in the art to achieve expression of a p16 is contemplated as well, provided that the levels of expression are sufficient for a given purpose.

By employing a promoter with well-known properties, the level and pattern of expression of a p16 following transfection can be optimized. For example, selection of a promoter which is active specifically in lung cells, such as tyrosinase (melanoma), alpha-fetoprotein and albumin (liver tumors), CC10 (lung tumor) and prostate-specific antigen (prostate tumor) will permit tissue-specific expression of a p16. Further, selection of a promoter that is regulated in response to specific physiologic signals can permit inducible expression of p16. For example, with the nucleic acid encoding p16 being expressed from the human PAI-1 promoter, expression is inducible by tumor necrosis factor. Tables 2 and 3 list several elements/promoters which may be employed, in the context of the present invention, to regulate the expression of p16. This list is not intended to be exhaustive of all the possible elements involved in the promotion of p16 expression but, merely, to be exemplary thereof.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Below is a list of viral promoters, cellular promoters/enhancers and inducible promoters/enhancers that could be used in combination with the nucleic acid encoding a p16 in an expression construct (Table 2 and Table 3). Additionally any promoter/enhancer combination (as per the Eukaryotic Promoter Data Base EPDB) could also be used to drive expression of a p16. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

TABLE 2

| ENHANCER |
| --- |
| Immunoglobulin Heavy Chain |
| Immunoglobulin Light Chain |
| T-Cell Receptor |
| HLA DQ α and DQ β |
| β-Interferon |
| Interleukin-2 |

TABLE 2-continued

| ENHANCER |
| --- |
| Interleukin-2 Receptor |
| MHC Class II $5_a^k$ |
| MHC Class II HLA-DRα |
| β-Actin |
| Muscle Creatine Kinase |
| Prealbumin (Transthyretin) |
| Elastase I |
| Metallothionein |
| Collagenase |
| Albumin Gene |
| α-Fetoprotein |
| τ-Globin |
| β-Globin |
| c-fos |
| c-HA-ras |
| Insulin |
| Neural Cell Adhesion Molecule (NCAM) |
| $α_{1-Antitrypsin}$ |
| H2B (TH2B) Histone |
| Mouse or Type I Collagen |
| Glucose-Regulated Proteins (GRP94 and GRP78) |
| Rat Growth Hormone |
| Human Serum Amyloid A (SAA) |
| Troponin I (TN I) |
| Platelet-Derived Growth Factor |
| Duchenne Muscular Dystrophy |
| SV40 |
| Polyoma |
| Retroviruses |
| Papilloma Virus |
| Hepatitis B Virus |
| Human Immunodeficiency Virus |
| Cytomegalovirus |
| Gibbon Ape Leukemia Virus |

TABLE 3

| Element | Inducer |
| --- | --- |
| MT II | Phorbol Ester (TFA) |
|  | Heavy metals |
| MMTV (mouse mammary tumor virus) | Glucocorticoids |
| β-Interferon | poly(rI)X |
|  | poly(rc) |
| Adenovirus 5 E2 | Ela |
| c-jun | Phorbol Ester (TPA), $H_2O_2$ |
| Collagenase | Phorbol Ester (TPA) |
| Stromelysin | Phorbol Ester (TPA), IL-1 |
| SV40 | Phorbol Ester (TFA) |
| Murine MX Gene | Interferon, Newcastle Disease Virus |
| GRP78 Gene | A23187 |
| α-2-Macroglobulin | IL-6 |
| Vimentin | Serum |
| MHC Class I Gene H-2kB | Interferon |
| HSP70 | Ela, SV40 Large T Antigen |
| Proliferin | Phorbol Ester-TPA |
| Tumor Necrosis Factor | FMA |
| Thyroid Stimulating Hormone α Gene | Thyroid Hormone |

In certain embodiments of the invention, the delivery of a nucleic acid in a cell may be identified in vitro or in vivo by including a marker in the expression construct. The marker would result in an identifiable change to the transfected cell permitting easy identification of expression. Usually the inclusion of a drug selection marker aids in cloning and in the selection of transformants. Alternatively, enzymes such as herpes simplex virus thymidine kinase (tk) (eukaryotic) or chloramphenicol acetyltransferase (CAT) prokaryotic) m ay be employed. Immunologic markers also can be employed. The selectable marker employed is not believed to be important, so long as it is capable of being expressed simultaneously with the nucleic acid encoding a p16. Further examples of selectable markers are well known to one of skill in the art.

Where a cDNA insert is employed, one will typically desire to include a polyadenylation signal to effect proper polyadenylation of the p16 transcript. The nature of the polyadenylation signal is not believed to be crucial to the successful practice of the invention, and any such sequence may be employed. The inventors have employed the SV40 polyadenylation signal in that it was convenient and known to function well in the target cells employed. Also contemplated as an element of the expression cassette is a terminator. These elements can serve to enhance message levels and to minimize read through from the cassette into other sequences.

In preferred embodiments of the invention, the expression construct comprises a virus or engineered construct derived from a viral genome. The ability of certain viruses to enter cells via receptor-mediated endocytosis and to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kilobases of foreign genetic material but can be readily introduced in a variety of cell lines and laboratory animals (Nicolas and Rubenstein, 1988; Temin, 1986).

(i) Retroviruses

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene, termed Ψ, functions as a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a p16 is inserted into the viral genome in the place of certain viral sequences to produce a virus that is replication-defective. In order to produce virions, a packaging cell line containing the gag, pol, and env genes but without the LTR and Ψ components is constructed (Mann et al., 1983). When a recombinant plasmid containing a human cDNA, together with the retroviral LTR and Ψ sequences is introduced into this cell line (by calcium phosphate precipitation for example), the Ψ sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

There are certain limitations to the use of retrovirus vectors in all aspects of the present invention. For example, retrovirus vectors usually integrate into random sites in the cell genome. This can lead to insertional mutagenesis through the interruption of host genes or through the insertion of viral regulatory sequences that can interfere with the function of flanking genes (Varmus et al., 1981). Another concern with the use of defective retrovirus vectors is the potential appearance of wild-type replication-competent virus in the packaging cells. This can result from recombination events in which the intact Ψ sequence from the recombinant virus inserts upstream from the gag, pol, env sequence integrated in the host cell genome. However, new packaging cell lines are now available that should greatly decrease the likelihood of recombination (Markowitz et al., 1988; Hersdorffer et al., 1990).

One limitation to the use of retrovirus vectors in vivo is the limited ability to produce retroviral vector titers greater than $10^6$ infectious U/mL. Titers 10- to 1,000-fold higher are necessary for many in vivo applications.

Several properties of the retrovirus have limited its use in lung cancer treatment (Stratford-Perricaudet and Perricaudet, 1991: (i) Infection by retrovirus depends on host cell division. In human cancer, very few mitotic cells can be found in tumor lesions (Warner and Heston, 1991). (ii) The integration of retrovirus into the host genome may cause adverse effects on target cells, because malignant cells are high in genetic instability. (iii) Retrovirus infection is often limited by a certain host range. (iv) Retrovirus has been associated with many malignancies in both mammals and vertebrates. (v) The titer of retrovirus, in general, is 100- to 1,000-fold lower than that of adenovirus.

(ii) Adenovirus

Knowledge of the genetic organization of adenovirus, a 36 kB, linear and double-stranded DNA virus, allows substitution of a large piece of adenoviral DNA with foreign sequences up to 7 kB (Grunhaus and Horwitz, 1992). In contrast to retrovirus, the infection of adenoviral DNA into host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in the human.

Adenovirus is particularly suitable for use as a gene transfer vector because of its mid-sized genome, ease of manipulation, high titer, wide target-cell range, and high infectivity. Both ends of the viral genome contain 100–200 base pair (bp) inverted terminal repeats (ITR), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression, and host cell shut off (Renan, 1990). The products of the late genes, including the majority of the viral capsid proteins, are expressed only after significant processing of a single primary transcript issued by the major late promoter (MLP). The MLP (located at 16.8 m.u.) is particularly efficient during the late phase of infection, and all the mRNAs issued from this promoter possess a 5' tripartite leader (TL) sequence which makes them preferred mRNAs for translation.

In the current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure. Use of the YAC system is an alternative approach for the production of recombinant adenovirus.

Generation and propagation of the current adenovirus vectors, which are replication deficient, depend on a unique helper cell line, designated 293, which was transformed from human embryonic kidney cells by Ad5 DNA fragments and constitutively expresses E1 proteins (Graham, et al., 1977). Since the E3 region is dispensable from the adenovirus genome (Jones and Shenk, 1978), the current adenovirus vectors, with the help of 293 cells, carry foreign DNA in either the E1, the E3 or both regions (Graham and Prevec, 1991). In nature, adenovirus can package approximately 105% of the wild-type genome (Ghosh-Choudhury, et al., 1987), providing capacity for about 2 extra kB of DNA. Combined with the approximately 5.5 kB of DNA that is replaceable in the E1 and E3 regions, the maximum capacity of the current adenovirus vector is under 7.5 kB, or about 15% of the total length of the vector. More than 80% of the adenovirus viral genome remains in the vector backbone and is the source of vector-borne cytotoxicity. Also, the replication deficiency of the E1 deleted virus is incomplete. For example, leakage of viral gene expression has been observed with the currently available adenovirus vectors at high multiplicities of infection (Mulligan, 1993).

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A-F. Adenovirus type 5 of subgroup C is the preferred starting material in order to obtain the conditional replication-defective adenovirus vector for use in the method of the present invention. This is because Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it will be most convenient to introduce the nucleic acid encoding p16 at the position from which the E1 coding sequences have been removed. However, the position of insertion of the p16 coding region within the adenovirus sequences is not critical to the present invention. The nucleic acid encoding a p16 transcription unit also may be inserted in lieu of the deleted E3 region in E3 replacement vectors as described previously by Karlsson et. al. (1986) or in the E4 region where a helper cell line or helper virus complements the E4 defect.

Adenovirus is easy to grow and manipulate and exhibits broad host range in vitro and in vivo. This group of viruses can be obtained in high titers, e.g., $10^9$–$10^{11}$ plaque-forming unit (PFU)/ml, and they are highly infective. The life cycle of adenovirus does not require integration into the host cell genome. The foreign genes delivered by adenovirus vectors are episomal, and therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus and Horwitz, 1992; Graham and Prevec, 1992). Recently, animal studies suggested that recombinant adenovirus could be used for gene therapy (Stratford-Perricaudet and Perricaudet, 1991; Stratford-Perricaudet et al., 1990; Rich et al., 1993). Experiments in administering recombinant adenovirus to different tissues include trachea instillation (Rosenfeld et al., 1991; Rosenfeld et al., 1992), muscle injection (Ragot et al., 1993), peripheral intravenous injection (Herz and Gerard, 1993), and stereotactic inoculation into the brain (Le Gal La Salle et al., 1993).

(iii) Other Viral Vectors as Expression Constructs

Other viral vectors may be employed as expression constructs in the present invention. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpesviruses may be employed. They offer several attractive features for various mammalian cells (Friedmann, 1989; Ridgeway, 1988; Baichwal and Sugden, 1986; Coupar et al., 1988; Horwich et al., 1990).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. The hepatotropism and persistence (integration) were particularly attractive properties for liver-directed gene transfer. Chang et al. recently introduced the chloramphenicol acetyltransferase (CAT) gene into duck hepatitis B virus genome in the place of the polymerase, surface, and pre-surface coding sequences. It was cotransfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

D. METHODS FOR GENE TRANSFER

In order to effect expression of sense or antisense p16 constructs, the expression construct must be delivered into a cell. This delivery may be accomplished in vitro, as in laboratory procedures for transforming cells lines, or in vivo or ex vivo (see below), as in the treatment of certain disease states. As described above, the preferred mechanism for delivery is via viral infection where the expression construct is encapsidated in an infectious viral particle.

Several non-viral methods for the transfer of expression constructs into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), and receptor-mediated transfection (Wu and Wu, 1987; Wu and Wu, 1988). Some of these techniques may be successfully adapted for in vivo or ex vivo use.

Once the expression construct has been delivered into the cell the nucleic acid encoding p16 may be positioned and expressed at different sites. In certain embodiments, the nucleic acid encoding p16 may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In one embodiment of the invention, the expression construct may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (1984) successfully injected polyomavirus DNA in the form of $CaPO_4$ precipitates into liver and spleen of adult and newborn mice demonstrating active viral replication and acute infection. Benvenisty and Neshif (1986) also demonstrated that direct intraperitoneal injection of $CaPO_4$ precipitated plasmids results in expression of the transfected genes. It is envisioned that DNA encoding a p16 may also be transferred in a similar manner in vivo and express p16.

Another embodiment of the invention for transferring a naked DNA expression construct into cells may involve particle bombardment. This method depends on the ability to accelerate DNA coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e., ex vivo treatment. Again, DNA encoding a p16 may be delivered via this method and still be incorporated by the present invention.

In a further embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

Liposome-mediated nucleic acid delivery and expression of foreign DNA in vitro has been very successful. Wong et al. (1980) demonstrated the feasibility of liposome-mediated delivery and expression of foreign DNA in cultured chick embryo, HeLa and hepatoma cells. Nicolau et al. (1987) accomplished successful liposome-mediated gene transfer in rats after intravenous injection.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention. Where a bacterial promoter is employed in the DNA construct, it also will be desirable to include within the liposome an appropriate bacterial polymerase.

Other expression constructs which can be employed to deliver a nucleic acid encoding a p16 into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise a ligand and a liposome. For example, Nicolau et al. (1987) employed lactosyl-ceramide, a galactose-terminal asialganglioside, incorporated into liposomes and observed an increase in the uptake of the insulin gene by hepatocytes. Thus, it is feasible that a nucleic acid encoding a p16 also may be specifically delivered into a cell type such as lung, epithelial or tumor cells, by any number of receptor-ligand systems with or without liposomes. For example, epidermal growth factor (EGF) may be used as the receptor for mediated delivery of a nucleic acid encoding a p16 in many tumor cells that exhibit upregulation of EGF receptor. Mannose can be used to target the mannose receptor on liver cells. Also, antibodies to CD5 (CLL), CD22 (lymphoma), CD25 (T-cell leukemia) and MAA (melanoma) can similarly be used as targeting moieties.

In certain embodiments, gene transfer may more easily be performed under ex vivo conditions. Ex vivo gene therapy refers to the isolation of cells from an animal, the delivery of a nucleic acid into the cells, in vitro, and then the return of the modified cells back into an animal. This may involve the surgical removal of tissue/organs from an animal or the primary culture of cells and tissues. Anderson et al., U.S. Pat. No. 5,399,346, and incorporated herein in its entirety, disclose ex vivo therapeutic methods.

Primary mammalian cell cultures may be prepared in various ways. In order for the cells to be kept viable while in vitro and in contact with the expression construct, it is necessary to ensure that the cells maintain contact with the correct ratio of oxygen and carbon dioxide and nutrients but are protected from microbial contamination. Cell culture techniques are well documented and are disclosed herein by reference (Freshner, 1992).

During in vitro culture conditions the expression construct may then deliver and express a nucleic acid encoding a p16 into the cells. Finally, the cells may be reintroduced into the original animal, or administered into a distinct animal, in a pharmaceutically acceptable form by any of the means described below. Thus, providing an ex vivo method of treating a mammal with a pathologic condition is within the scope of the invention.

E. p16 EXPRESSION CONSTRUCTS IN COMBINATION WITH OTHER THERAPIES

Tumor cell resistance to DNA damaging agents represents a major problem in clinical oncology. One goal of current cancer research is to find ways to improve the efficacy of chemo- and radiotherapy by combining it with gene therapy. For example, the herpes simplex-thymidine kinase (HS-tK) gene, when delivered to brain tumors by a retroviral vector system, successfully induced susceptibility to the antiviral agent ganciclovir (Culver, et al., 1992). In the context of the present invention, it is contemplated that p16 replacement therapy could be used similarly in conjunction with chemo- or radiotherapeutic intervention.

To kill cells, such as malignant or metastatic cells, using the methods and compositions of the present invention, one would generally contact a "target" cell with a p16 expression construct and at least one DNA damaging agent. These compositions would be provided in a combined amount effective to kill or inhibit proliferation of the cell. This process may involve contacting the cells with the p16 expression construct and the DNA damaging agent(s) or factor(s) at the same time. This may be achieved by contacting the cell with a single composition or pharmacological formulation that includes both agents, or by contacting the cell with two distinct compositions or formulations, at the same time, wherein one composition includes the p16 expression construct and the other includes the DNA damaging agent.

Alternatively, the p16 treatment may precede or follow the DNA damaging agent treatment by intervals ranging from minutes to weeks. In embodiments where the DNA damaging factor and p16 expression construct are applied separately to the cell, one would generally ensure that a significant period of time did not expire between the time of each delivery, such that the DNA damaging agent and p16 expression construct would still be able to exert an advantageously combined effect on the cell. In such instances, it is contemplated that one would contact the cell with both agents within about 12–24 hours of each other and, more preferably, within about 6–12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either p16 or the DNA damaging agent will be desired. Various combinations may be employed, where p16 is "A" and the DNA damaging agent is "B":

```
A/B/A    B/A/B B/B/A A/A/B    B/B/B/A B/B/A/B
A/A/B/B A/B/A/B A/B/B/A B/B/A/A B/A/B/A B/A/A/B
A/A/A/B B/A/A/A A/B/A/A A/A/B/A A/B/B/B B/A/B/B
```

To achieve cell killing, both agents are delivered to a cell in a combined amount effective to kill the cell.

DNA damaging agents or factors are defined herein as any chemical compound or treatment method that induces DNA damage when applied to a cell. Such agents and factors include radiation and waves that induce DNA damage such as, γ-irradiation, X-rays, UV-irradiation, microwaves, electronic emissions, and the like. A variety of chemical compounds, also described as "chemotherapeutic agents", function to induce DNA damage, all of which are intended to be of use in the combined treatment methods disclosed herein. Chemotherapeutic agents contemplated to be of use, include, e.g., adriamycin, 5-fluorouracil (5FU), etoposide (VP-16), camptothecin, actinomycin-D, mitomycin C, cisplatin (CDDP) and even hydrogen peroxide. The invention also encompasses the use of a combination of one or more DNA damaging agents, whether radiation-based or actual compounds, such as the use of X-rays with cisplatin or the use of cisplatin with etoposide. In certain embodiments, the use of cisplatin in combination with a p16 expression construct is particularly preferred as this compound.

In treating cancer according to the invention, one would contact the tumor cells with a DNA damaging agent in addition to the p16 expression construct. This may be achieved by irradiating the localized tumor site with DNA damaging radiation such as X-rays, UV-light, γ-rays or even microwaves. Alternatively, the tumor cells may be contacted with the DNA damaging agent by administering to the subject a therapeutically effective amount of a pharmaceutical composition comprising a DNA damaging compound such as, adriamycin, 5-fluorouracil, etoposide, camptothecin, actinomycin-D, mitomycin C, or more preferably, cisplatin. The DNA damaging agent may be prepared and used as a combined therapeutic composition, or kit, by combining it with a p16 expression construct, as described above.

Agents that directly cross-link nucleic acids, specifically DNA, are envisaged and are shown herein, to eventuate DNA damage leading to a synergistic antineoplastic combination. Agents such as cisplatin, and other DNA alkylating may be used. Cisplatin has been widely used to treat cancer, with efficacious doses used in clinical applications of 20 mg/m$^2$ for 5 days every three weeks for a total of three courses. Cisplatin is not absorbed orally and must therefore be delivered via injection intravenously, subcutaneously, intratumorally or intraperitoneally.

Agents that damage DNA also include compounds that interfere with DNA replication, mitosis and chromosomal segregation. Such chemotherapeutic compounds include adriamycin, also known as doxorubicin, etoposide, verapamil, podophyllotoxin, and the like. Widely used in a clinical setting for the treatment of neoplasms, these compounds are administered through bolus injections intravenously at doses ranging from 25–75 mg/m$^2$ at 21 day intervals for adriamycin, to 35–50 mg/m$^2$ for etoposide intravenously or double the intravenous dose orally.

Agents that disrupt the synthesis and fidelity of nucleic acid precursors and subunits also lead to DNA damage. As such a number of nucleic acid precursors have been developed. Particularly useful are agents that have undergone extensive testing and are readily available. As such, agents such as 5-fluorouracil (5-FU), are preferentially used by neoplastic tissue, making this agent particularly useful for targeting to neoplastic cells. Although quite toxic, 5-FU, is applicable in a wide range of carriers, including topical, however intravenous administration with doses ranging from 3 to 15 mg/kg/day being commonly used.

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage DNA, on the precursors of DNA, the replication and repair of DNA, and the assembly and maintenance of chromosomes. Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

The skilled artisan is directed to "Remington's Pharmaceutical Sciences" 15th Edition, chapter 33, in particular pages 624–652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

The inventors propose that the regional delivery of p16 expression constructs to patients with p16-linked cancers will be a very efficient method for delivering a therapeutically effective gene to counteract the clinical disease. Similarly, the chemo- or radiotherapy may be directed to a particular, affected region of the subjects body. Alternatively, systemic delivery of p16 expression construct or the DNA damaging agent may be appropriate in certain circumstances, for example, where extensive metastasis has occurred.

In addition to combining p16-targeted therapies with chemo- and radiotherapies, it also is contemplated that combination with other gene therapies will be advantageous. For example, targeting of p16 and p53 mutations at the same time may produce an improved anti-cancer treatment. Any other tumor-related gene conceivably can be targeted in this manner, for example, p21, Rb, APC, DCC, NF-1, NF-2, WT-1, MEN-I, MEN-II, BRCA1, VHL, FCC, MCC, ras, myc, neu, raf, erb, src, fms, jun, trk, ret, gsp, hst, bcl and abl.

F. NUCLEIC ACID ENCODING p16 OR p16 AS MARKERS

In certain embodiments, a nucleic acid encoding a p16 or p16 peptide may be employed for diagnostic purposes. The absence or reduced/increased level of p16 nucleic acid encoding a p16 may be indicative of a disease state such as cancer. Thus, the present invention also includes using nucleic acid encoding a p16 or p16 as a marker. There are numerous methods, well known to one of skill in the art, that may be employed in detecting a nucleic acid encoding p16 or a p16. Two common methods for detecting nucleic acids encoding a p16 are Southern and Northern analyses and variations thereof. The level of p16 message can be used as a marker to indicate tumorigenicity.

An alternative approach would be to detect p16 with immunoassays using antibodies that bind to p16 in Western Blotting and FACS analysis are also described in Example I. Both techniques were employed to detect p16 expression on the cell surface. It will be readily appreciated that detection is not limited to the above techniques, and that there are numerous other methods which may be encompassed by the present invention.

Other, preferred immunoassays are the various types of enzyme-linked immunosorbent assays (ELISA's) and radioimmunoassays (RIA's) known in the art. Immunohistochemical detection using tissue sections also is particularly useful.

In ELISA's, an anti-p16 antibody (such as Ab669, as disclosed herein) is immobilized onto a selected surface exhibiting protein affinity, such as a well in a polystyrene microtiter plate. Then, a test composition containing the cells or cellular material, such as a clinical sample, is added to the wells. After binding and washing to remove non-specifically bound immunocomplexes, the bound p16 may be detected. Detection is generally achieved by the addition of another anti-p16 antibody that is linked to a detectable label. This type of ELISA is a simple "sandwich ELISA". Detection may also be achieved by the addition of a second anti-p16 antibody, followed by the addition of a third antibody that has binding affinity for the second anti-p16 antibody, with the third antibody being linked to a detectable label.

In another exemplary ELISA, the samples containing the cellular material to be tested for the level of p16, are immobilized onto the well surface and then contacted with the anti-p16 antibodies. After binding and appropriate washing, the bound immunocomplexes are detected. Where the initial anti-p16 antibodies are linked to a detectable label, the immunocomplexes may be detected directly. Again, the immunocomplexes may be detected using a second antibody that has binding affinity for the first anti-p16 antibody, with the second antibody being linked to a detectable label.

Competition ELISA's also are possible in which test samples compete for binding with known amounts of labeled p16 antigens or antibodies. The amount of reactive species in the unknown sample is determined by mixing the sample with the known labeled species before or during incubation with coated wells. The presence of reactive species in the sample acts to reduce the amount of labeled species available for binding to the well and thus reduces the ultimate signal.

Irrespective of the format employed, ELISA's have certain features in common, such as coating, incubating or binding, washing to remove non-specifically bound species, and detecting the bound immunocomplexes. These are described as follows:

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein, gelatin, and solutions of milk powder. The blocking solutions also usually contain the detergent Tween-20, which greatly helps to reduce non-specific binding. The coating allows for blocking of nonspecific adsorption sites on the immobilizing surface and thus reduces the background caused by nonspecific binding of antisera onto the surface.

In ELISA's, it is more customary to use a secondary or tertiary detection means rather than a direct procedure. Thus, after binding of the p16 or anti-p16 antibody to the well, coating with a non-reactive material to reduce background, and washing to remove unbound material, the immobilizing surface is contacted with the clinical or biological sample to be tested under conditions effective to allow immunocomplex (antigen/antibody) formation. Detection of the immunocomplex then requires a labeled secondary binding ligand or antibody, or a secondary binding ligand or antibody in conjunction with a labeled tertiary antibody or third binding ligand.

"Under conditions effective to allow immunocomplex (antigen/antibody) formation" means that the conditions preferably include diluting the antigens and antibodies with solutions such as BSA, bovine gamma globulin (BGG) and phosphate buffered saline (PBS)/Tween-20. These added agents also tend to assist in the reduction of nonspecific background.

The suitable conditions also mean that the incubation is at a temperature and for a period of time sufficient to allow effective binding. Incubation steps are typically from about 1 to 2 to 4 hours, at temperatures preferably on the order of 25° to 27° C., or may be overnight at about 4° C. or so.

Following all incubation steps in an ELISA, the contacted surface is washed so as to remove non-complexed material. Washing often includes washing with a solution of PBS/Tween-20, or borate buffer. Following the formation of specific immunocomplexes between the test sample and the originally bound material, and subsequent washing, the occurrence of even minute amounts of immunocomplexes may be determined.

To provide a detecting means, the second or third antibody will have an associated label to allow detection. Preferably, this will be an enzyme that will generate color development upon incubating with an appropriate chromogenic substrate. Thus, for example, one will desire to contact and incubate the first or second immunocomplex with a urease, glucose oxidase, alkaline phosphatase or hydrogen peroxidase-conjugated antibody for a period of time and under conditions that favor the development of further immunocomplex formation (e.g., incubation for 2 hours at room temperature in a PBS-containing solution such as PBS/Tween-20).

After incubation with the labeled antibody, and subsequent to washing to remove unbound material, the amount of label is quantified, e.g., by incubation with a chromogenic substrate such as urea and bromocresol purple or 2,2'-azino-di-(3-ethyl-benzthiazoline-6-sulfonic acid (ABTS) and $H_2O_2$, in the case of peroxidase as the enzyme label. Quantification is then achieved by measuring the degree of color generation, e.g., using a visible spectra spectrophotometer.

F. PHARMACEUTICAL COMPOSITIONS AND ROUTES OF ADMINISTRATION

Where clinical application of an expression construct comprising a nucleic acid encoding p16 is contemplated, it will be necessary to prepare the complex as a pharmaceutical composition appropriate for the intended application. Generally this will entail preparing a pharmaceutical composition that is essentially free of pyrogens, as well as any other impurities that could be harmful to humans or animals. One also will generally desire to employ appropriate salts and buffers to render the complex stable and allow for complex uptake by target cells.

Aqueous compositions of the present invention comprise an effective amount of the expression construct and nucleic acid, dissolved or dispersed in a pharmaceutically acceptable carrier or aqueous medium. Such compositions can also be referred to as inocula. The phrases "pharmaceutically or pharmacologically acceptable" refer to molecular entities and compositions that do not produce an adverse, allergic or other untoward reaction when administered to an animal, or a human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients also can be incorporated into the compositions.

Solutions of the active compounds as free base or pharmacologically acceptable salts can be prepared in water suitably mixed with a surfactant, such as hydroxypropylcellulose. Dispersions also can be prepared in glycerol, liquid polyethylene glycols, and mixtures thereof and in oils. Under ordinary conditions of storage and use, these preparations contain a preservative to prevent the growth of microorganisms.

The expression constructs and delivery vehicles of the present invention may include classic pharmaceutical preparations. Administration of therapeutic compositions according to the present invention will be via any common route so long as the target tissue is available via that route. This includes oral, nasal, buccal, rectal, vaginal or topical. Topical administration would be particularly advantageous for treatment of skin cancers, to prevent chemotherapy-induced alopecia or other dermal hyperproliferative disorder. Alternatively, administration will be by orthotopic, intradermal subcutaneous, intramuscular, intraperitoneal or intravenous injection. Such compositions would normally be administered as pharmaceutically acceptable compositions that include physiologically acceptable carriers, buffers or other excipients.

The therapeutic compositions of the present invention are advantageously administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain 10 mg, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers and the like. Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components the pharmaceutical composition are adjusted according to well known parameters.

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders. When the route is topical, the form may be a cream, ointment, salve or spray.

An effective amount of the therapeutic agent is determined based on the intended goal, for example (i) inhibition of tumor cell proliferation or (ii) elimination of tumor cells. The term "unit dose" refers to physically discrete units suitable for use in a subject, each unit containing a predetermined-quantity of the therapeutic composition calculated to produce the desired responses, discussed above, in association with its administration, i.e., the appropriate route and treatment regimen. The quantity to be administered, both according to number of treatments and unit dose, depends on the subject to be treated, the state of the subject and the protection desired. Precise amounts of the therapeutic composition also depend on the judgment of the practitioner and are peculiar to each individual.

G. KITS

All the essential materials and reagents required for inhibiting tumor cell proliferation, transforming cells or detecting cancer cells, may be assembled together in a kit. This generally will comprise selected expression constructs. Also included may be various media for replication of the expression constructs and host cells for such replication. Such kits will comprise distinct containers for each individual reagent.

When the components of the kit are provided in one or more liquid solutions, the liquid solution preferably is an aqueous solution, with a sterile aqueous solution being particularly preferred. For in vivo use, the expression construct may be formulated into a pharmaceutically acceptable syringeable composition. In this case, the container means may itself be an inhalent, syringe, pipette, eye dropper, or other such like apparatus, from which the formulation may be applied to an infected area of the body, such as the lungs, injected into an animal, or even applied to and mixed with the other components of the kit.

The components of the kit may also be provided in dried or lyophilized forms. When reagents or components are provided as a dried form, reconstitution generally is by the addition of a suitable solvent. It is envisioned that the solvent also may be provided in another container means.

The kits of the present invention also will typically include a means for containing the vials in close confinement for commercial sale such as, e.g., injection or blow-molded plastic containers into which the desired vials are retained.

Irrespective of the number or type of containers, the kits of the invention also may comprise, or be packaged with, an instrument for assisting with the injection/administration or placement of the ultimate complex composition within the body of an animal. Such an instrument may be an inhalent, syringe, pipette, forceps, measured spoon, eye dropper or any such medically approved delivery vehicle.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

A. MATERIALS AND METHODS

Cell Lines. Cell line 293 was maintained in Eagle's modified essential medium supplemented with 10% heat-inactivated horse serum. Human NSCLC cell lines H226Br, H322 were grown in RPMI medium containing 5% fetal bovine serum. Human normal breast cell line HBL100 was grown in F12 medium supplemented with 10% fetal bovine serum.

$p16^{INK4}$ cDNA Subcloning. The original $p16^{INK4}$ cDNA was amplified from the total RNA of normal human lymphocytes by RT-PCR™ using the primers 5'-ATGGAGCCTTCGGC TGACTGG-3' (SEQ ID NO:3) and 5'-CCTGTAGGACCTTCGGTGACT-3' (SEQ ID NO:4). The PCR™ product was subcloned in pCR™ vector (Invitrogen, San Diego, Calif.) and verified by double-stranded DNA sequencing. Because of a correction of the $p16^{INK4}$ cDNA sequence in GenBank, an additional sequence of 42 base pairs was added later to the 5' end of the cloned $p16^{INK4}$ cDNA by two PCR™ steps. The first PCR™ step used primer A (5'-GATCCGGCGG CGGGGAGCAG-CATGGAGCCTTC GGCTGACTGG-3'; SEQ ID NO:5); and primer C (5'-GCCTCTCTGGTTCTTTCA-3'; SEQ ID NO:6). The second PCR™ step used primer B (5'-CGGGCGGGGAGCAGCATGGAGCCGG CGGCGGGGAGC-3'; SEQ ID NO:7) and primer C. The final wild-type $p16^{INK4}$ cDNA sequence in the pCR™ vector pCR-p-16) was again verified by double-stranded DNA sequencing.

pAd-p16 Construction. The shuttle vector pEC53 (Zhang et al., 1994) was digested by restriction enzymes HinD III AND Hpa I. The vector backbone was separated from p53 cDNA by running the digested DNA through 1% agarose gel and was purified from the gel. $p16^{INK4}$ cDNA was excised from pCR-p16 and ligated to the purified shuttle vector backbone. The final product, pAd-p16, carries the $p16^{INK4}$ expression cassette which contains human CMV promoter (Boshart et al., 1985) wild-type $p16^{INK4}$ cDNA, and SV40 early polyadenylation signal.

Generation of Recombinant p16$^{INK4}$ Adenovirus. The recombinant Ad5CMV-lacZ adenovirus DNA was digested with restriction enzymes XbaI and ClaI and the 32 kb partial adenovirus DNA fragment was purified in a 0.3% agarose gel. This DNA fragment and pAd-p16 plasmid DNA were cotransfected into 293 cells by CaPO$_4$-mediated transfection. The transfected cells were maintained in medium until the onset of the cytopathic effect. The newly generated p16$^{INK4}$ recombinant adenovirus (Ad-p16) was identified by PCR™ analysis of the DNA samples prepared from the cell culture supernatant. The recombinant adenovirus Ad5 CMV-lacZ which carries the lacZ gene of E. coli, has a structure similar to that of Ad-p16 and was used as a control in these studies.

Viral Stocks, Titers, and Infection. Individual clones of the Ad-p16 and Ad5CMV-lacZ viruses were obtained by plaque-purification and were propagated in 293 cells according to the method of Graham and Prevec (1991). The viral titers were determined by plaque assays. The cell lines were infected by addition of the viral solutions to cell monolayers and incubation at room temperature for 30 min with brief agitation every 5 min. This was followed by the addition of culture medium and return of the infected cells to the 37° C. incubator.

Tumorigenicity Assays. H460 cells were infected with Ad-p16 or Ad5CMV-lacZ at an MOI of 50 PFU/cell. An equal number of cells were treated with medium only as a mock infection. Twenty-four hours after infection, the treated cells were harvested and rinsed twice with PBS. For each treatment, 5×10$^6$ cells in a volume of 0.1 ml of PBS were injected subcutaneously into the dorsal flank of BALB/c nu/nu mice (Harlan Sprague-Dawley Co., Houston, Tex.). The treated mice were examined weekly after injection. Tumor generation was evaluated at the end of a 3-week period. Tumor volume was calculated by assuming a spherical shape with the average tumor diameter calculated as the square root of the product of orthogonal diameters.

B. RESULTS

Generation of the Ad-p16 Recombinant Virus. One of the advantages of adenovirus as a gene transfer vector is that it has high infectivity in a wide range of host cells (Berkner, 1988). An adenovirus-derived shuttle vector for human cancer gene therapy, pEC53, was constructed previously (Zhang et al., 1994). A recombinant virus derived from this vector, Ad5CMV-p53, has an infectivity of 97% to 100% in several lung cancer cell lines (Zhang et al., 1994), including H460, H322, and H226Br. In this study, the p53 gene in pEC53 was replaced by the full-length p16$^{INK4}$ cDNA. The final product, pAd-p16, carries the p16$^{INK4}$ gene expression cassette which contains a human CMV promoter (Boshart et al., 1985), wild-type p16$^{INK4}$ cDNA, and a SV40 early polyadenylation signal. A 32 kB partial fragment of adenovirus DNA generated by Xba I digestion of the DNA of a recombinant virus, Ad5CMV-lacZ, was cotransfected with pAd-p16 plasmid into 293 cells for homologous recombination. The recombinant viral product, Ad-p16, has a genomic structure similar to that of Ad5CMV-lacZ except that the lacZ gene is replaced by the p16$^{INK4}$ gene. Since the E1 regions of the recombinant adenoviruses are substituted by the p16$^{INK4}$ gene or the lacZ gene expression cassette, they can be propagated only in 293 cells that complement the E1 deletion. Ad5CMV-lacZ was used as a viral control for Ad-p16.

Expression of Exogenous p16$^{INK4}$ Protein in Human Lung Cancer Cells. Three human NSCLC cell lines were chosen for this study: H460, H322 and H226Br. H460 carries homozygous p16$^{INK4}$ gene deletions (Kamb et al., 1994), but the p53 gene (Takahashi et al., 1989) and the Rb gene (Harbour et al., 1988) are wild-type. H322 carries a homozygous p16$^{INK4}$ gene deletion (Okamoto et al., 1994), a wild-type Rb gene (Harbour et al., 1988), and a homozygous p53 mutation at codon 248 (Mitsudomi et al., 1992). H226Br carries the p16$^{INK4}$ gene detected by southern blot and PCR™ analysis which has not been sequenced, but does not express p16$^{INK4}$ at the protein level. It carries a homozygous p53 mutation at codon 254 (Fujiwara et al., 1994) and expresses wild-type Rb protein (Harbour et al., 1988). A cultured normal human breast epithelial cell line, HBL100, expresses wild-type p16$^{INK4}$, wild-type p53 and wild-type RB gene and was used in this study as a normal cell line control. Only cell line HBL100 expressed p16$^{INK4}$ protein before viral infection. To obtain a high level of expression of exogenous p16$^{INK4}$ protein, the human CMV promoter (Boshart et al., 1985) was used to drive the expression of the p16$^{INK4}$ gene. High levels of exogenous p16$^{INK4}$ protein expression were achieved in the H460, H322 and H226Br cells after infection with Ad-p16. The level of p16$^{INK4}$ protein in HBL100 was much higher after Ad-p16 infections, indicating exogenous p16$^{INK4}$ protein expression in this cell line. Subsequently, the effect(s) of this introduced p16$^{INK4}$ protein on the tumor cell lines were examined in the following assays.

Effect of p16$^{INK4}$ Protein on Lung Cancer Cell Growth. The NSCLC cell lines H460, H322 and H226Br and the normal breast cell line HBL100 were infected with Ad-p16 or Ad5CMV-lacZ at 50 PFU/cell. Triplicate sets of the infected and mock-infected cells were counted every day for 6 days, and the mean cell number for each day was calculated. As shown in FIG. 2, growth rates of the Ad-p16-infected H460, H322 and H226Br cells were inhibited by 94%, 85%, and 97%, respectively, compared with that of the Ad5CMV-lacZ-infected cells. However, the growth rate of HBL100 infected with Ad-p16 was inhibited by less than 3% when compared with that of the Ad5CMV-lacZ-infected HBL100 cells. This suggested that introduction of the p16$^{INK4}$ gene into these cell lines could specifically suppress cell proliferation by restoring p16$^{INK4}$ expression. The growth rates of the Ad5CMV-lacZ-treated cells were lower than those of the mock-infected cells for all the cell lines, indicating cytotoxicity caused by expressed viral proteins and the lacZ gene. This virus-related cytotoxicity was increased when a higher MOI was used. The cell lines had differing sensitivities to this effect.

Cell-Cycle Arrest Mediated by Ad-p16. It is known that the p16$^{INK4}$ protein can inhibit the activity of CDK4 and CDK6, thereby blocking the entry of the proliferating cells from G$_1$ phase to S phase (Serrano et al., 1993; Serrano et al., 1995). To examine the mechanism of the growth rate inhibition mediated by Ad-p16, H460, H322, H226Br and HBL100 cells were infected as described in the growth rate assay and harvested 24 hours after infection for cell cycle analysis by flow cytometry. As shown in Table 4, Ad-p16-mediated expression of the p16$^{INK4}$ protein significantly increased the numbers of cells in G$_1$ phase and decreased the number of cells in S and (G$_2$+M) phases in the p16$^{INK4}$ deleted tumor cell lines, suggesting the induction of G$_1$ arrest. In contrast, no G$_1$ arrest was observed in the p16$^{INK4}$ protein-positive normal breast cell line, HBL100. These results suggest that the p16$^{INK4}$ protein suppresses the growth of the tumor cells by mediating G$_1$ arrest in cell lines that do not express p16$^{INK4}$.

TABLE 4

Flow Cytometry Analysis of Cell-Cycle Effects of p16$^{INK4}$ Mediated by Ad-p16

| cell types & infected viruses | Percent of Cells in | | |
|---|---|---|---|
| | $G_0/G_1$ | S | $G_2/M$ |
| HBL100/Ad-p16 | 36 | 42 | 22 |
| HBL100/Ad5CMV-lacZ | 31 | 44 | 25 |
| HBL100/medium | 31 | 42 | 27 |
| H460/Ad-p16 | 88 | 9 | 3 |
| H460/Ad5CMV-lacZ | 41 | 32 | 27 |
| H460/medium | 39 | 35 | 26 |
| H322/Ad-p16 | 80 | 6 | 14 |
| H322/Ad5CMV-lacz | 30 | 36 | 34 |
| H322/medium | 30 | 36 | 34 |
| H226Br/Ad-p16 | 80 | 11 | 9 |
| H226Br/Ad5CMV-lacZ | 20 | 53 | 27 |
| H226Br/medium | 26 | 44 | 30 |

Values are shown for a representative assay. Cells were infected the same way as in the cell growth rate determination assay. 24 hours after infection, cells were treated with 1% Tween-20 and stained with propidium iodide and then analyzed by flow cytometry for DNA synthesis and cell cycle status. Flow cytometric assay was performed with a FACScan (Becton Dickinson, San Jose, CA) equipped with an air-cooled 15-mW 488 nm argon laser. Red fluorescence was measured through a long pass filter with cut-off wavelength at 650 nm.

Inhibition of Tumorigenicity Mediated by Ad-p16. To determine whether the Ad-p16 virus can inhibit tumorigenicity of human NSCLC cells, BALB/c nu/nu mice were injected subcutaneously with H460 cells to induce tumor formation. Each mouse received one injection of 5×10$^6$ cells that had been infected with either Ad-p16 or Ad5CMV-lacZ at 50 PFU/cell for 24 hours. H460 cells treated with medium alone were used as mock-infected controls. Each treatment was given to four mice. The mice were observed, and when tumors appeared they were measured for a 3-week period. Two independent studies were done to confirm reproducibility and the data from both studies are summarized in Table 5. Ad-p16 treated cells significantly suppressed tumor growth in vivo. 100% of the mice that received medium treated cells and 87.5% of the mice that received Ad5/CMV-lacZ treated cells developed tumors. On the other hand, only 50% mice in both studies that received Ad-p16 treated cells developed tumors and the mean volume was only 11% of that in Ad5CMV-lacZ virus treated mice and 6% of that in the medium treated mice (p<0.001 by two sided student's T test). Thus, the tumorigenicity of the lung cancer cells was inhibited by prior treatment with Ad-p16, indicating that the p16$^{INK4}$ protein may have therapeutic efficacy.

TABLE 5

Effect of p16$^{INK4}$ on Tumorigenicity of H460 Cell Line in Nude Mice

| | Treatment | No. of tumors No. of mice (%) | Mean Volume (mm$^3$ ± SD) |
|---|---|---|---|
| Experiment 1 | Medium | 4/4 (100%) | 1047.3 ± 104.7 |
| | Ad5/CMV-LacZ | 4/4 (100%) | 740.5 ± 205.5 |
| | Ad-p16 | 0/4 (0%) | — |
| Experiment 2 | Medium | 4/4 (100%) | 1158.6 ± 200.2 |
| | Ad5/CMV-LacZ | 3/4 (75%) | 658.3 ± 144.3 |
| | Ad-p16 | 4/4 (100%) | 71.2 ± 19.6 |

The H460 cells were infected with viruses at a MOI of 50 PFU/cell for 24 hours and injected subcutaneously at 5 × 10$^6$ cells/mouse. Tumor sizes were determined at the end of a three-week period.

The therapeutic potential for Ad-p16 was examined in a BALB/c nu/nu mouse model. Subcutaneous tumor nodules arose 20 days after injecting mice subcutaneously with 5×10$^6$ H460 cells. The resulting tumors were directly injected with Ad-p16 (10$^{10}$ PFU/tumor), Ad5CMV-lacZ (1010 PFU/tumor) or PBS. As shown in FIG. 3, 18 days after injection the average volume of Ad-p16-treated tumors was only 49% of that of the control virus-treated tumors and 34% of that of the tumors injected with PBS (p<0.001 by two-sided Student's t test).

REFERENCES

The following references, to the extent that they provide exemplary procedural or other details supplementary to those set forth herein, are specifically incorporated herein by reference.

Anderson et al. U.S. Pat. No. 5,399,346, 1995.

Arap et al., "Replacement of the p16/CDKN2 gene suppresses human glioma cell growth," *Cancer Res.*, 55:1351–1354, 1995.

Baichwal and Sugden, "Vectors for gene transfer derived from animal DNA viruses: Transient and stable expression of transferred genes," In: Kucherlapati R, ed. Gene transfer. New York: Plenum Press, pp. 117–148, 1986.

Benvenisty and Neshif, "Direction introduction of genes into rats and expression of the genes," *Proc. Nat. Acad. Sci. USA*, 83:9551–9555, 1986.

Berkner, "Development of adenovirus vectors for the expression of heterologous genes," *BioTechniques*, 6:616–629, 1988.

Boshart et al., "A very strong enhancer is located upstream of an immediate early gene of human cytomegalovirus," *Cell*, 41:521–530, 1985.

Cairns et al., "Rates of p16 (MTS1) mutations in primary tumors with 9p loss," *Science*, 265:416, 1994.

Caldas et al., "Frequent somatic mutations and homozygous deletions of the p16 (MTS1) gene in pancreatic adenocarcinoma," *Nat. Genet.*, 8:27–32, 1994.

Chang et al., "foreign gene delivery and expression in hepatocytes using a hepatitis B virus vector," *Hepatology*, 14:124A, 1991.

Chen and Okayama, "High-efficiency transfection of mammalian cells by plasmid DNA," *Mol. Cell Biol.*, 7:2745–2752, 1987.

Cheng et al., "p16 alterations and deletion mapping of 9p21–p22 in malignant mesothelioma," *Cancer Res.*, 54:5547–5551, 1994.

Chomcyzynski and Sacchi, "Single-step method of RNA isolation by acid guanidinium thiocyanate-phenol-chloroform extraction," *Anal. Biochem.*, 162:156–159, 1987.

Coffin, "Retroviridae and their replication," In: Fields B N, Knipe D M, ed. Virology. New York: Raven Press, pp. 1437–1500, 1990.

Couch et al., "Immunization with types 4 and 7 adenovirus by selective infection of the intestinal tract," *Am. Rev. Resp. Dis.*, 88:394–403, 1963.

Coupar et al., "A general method for the construction of recombinant vaccinia virus expressing multiple foreign genes," *Gene*, 68:1–10, 1988.

Culver et al., "In vivo gene transfer with retroviral vector-producer cells for treatment of experimental brain tumors," *Science*, 256:1550–1552, 1992.

Davis et al., "DNA preparation from cultured cells and tissue," In: Davis, L. G., Dibner, M. D., and Battey, J. F. (eds.), Basic Methods in Molecular Biology, New York: Elsevier, pp. 47–50, 1986.

Dubensky et al., "Direct transfection of viral and plasmid DNA into the liver or spleen of mice," *Proc. Nat. Acad. Sci. USA*, 81:7529–7533, 1984.

Fearon et al., *Science*, 247:49, 1990.

Fechheimer et al., "Transfection of mammalian cells with plasmid DNA by scrape loading and sonication loading," *Proc. Natl. Acad. Sci. USA*, 84:8463–8467, 1987.

Fraley et al., "Entrapment of a bacterial plasmid in phospholipid vesicles: Potential for gene transfer," *Proc. Natl. Acad. Sci. USA*, 76:3348–3352, 1979.

Freshner, R. I. "Animal Cell Culture: a Practical Approach", Second Edition, Oxford/New York, IRL Press, Oxford University Press, 1992.

Freshner, "Culture of Animal Cells: A Manual of Basic Technique," 2nd ed., New York, A. R. Liss, 1987.

Friedmann, "Progress toward human gene therapy," *Science*, 244:1275–1281, 1989.

Fujiwara et al., "Therapeutic effect of a retroviral wild-type p53 expression vector in an orthotopic lung cancer model," *JNCI*, 86:1458–1462, 1994.

Ghosh and Bachhawat, "Targeting of liposomes to hepatocytes," In: Wu G, Wu C ed. Liver diseases, targeted diagnosis and therapy using specific receptors and ligands. New York: Marcel Dekker, pp. 87–104, 1991.

Ghosh-Choudhury et al., "Protein IX, a minor component of the human adenovirus capsid, is essential for the packaging of full-length genomes," *EMBO J.*, 6:1733–1739, 1987.

Gleave et al., "Acceleration of human prostate cancer growth in vivo by factors produced by prostate and bone fibroblasts," *Cancer Res.*, 51:3753–3761, 1991.

Gomez-Foix et al., "Adenovirus-mediated transfer of the muscle glycogen phosphorylase gene into hepatocytes confers altered regulation of glycogen," *J. Biol. Chem.*, 267:25129–25134, 1992.

Gopal, "Gene transfer method for transient gene expression, stable transfection, and cotransfection of suspension cell cultures," *Mol. Cell Biol.*, 5:1188–1190, 1985.

Graham and Prevec, "Manipulation of adenovirus vector," In: E. J. Murray (ed.), Methods in Molecular Biology: Gene Transfer and Expression Protocol, Clifton, N.J.: Humana Press, 7:109–128, 1991.

Graham and van der Eb, "A new technique for the assay of infectivity of human adenovirus 5 DNA", *Virology*, 52:456–467, 1973.

Graham et al., "Characteristics of a human cell line transformed by DNA from human adenovirus type 5", *J. Gen. Virol.*, 36:59–72, 1977.

Graham and Prevec, "Adenovirus-based expression vectors and recombinant vaccines," *Biotechnology*, 20:363–390, 1992.

Gruis et al., "Genetic evidence in melanoma and bladder cancers that p16 and p53 function in separate pathways of tumor suppression," *Am. J. Pathol.*, 146:1199–1206, 1995.

Grunhaus and Horwitz, "Adenovirus as cloning vector," *Seminar in Virology*, 3:237–252, 1992.

Grunicke and Maly, "Role of GTPase and GTPase regulatory proteins in oncogenesis," *Crit. Rev. Oncog.*, 4:389–402, 1993.

Harbour et al., "Abnormalities in structure and expression of the human retinoblastoma gene in SCLC," *Science*, 241:353–357, 1988.

Harland and Weintraub, "Translation of mammalian mRNA injected into Xenopus oocytes is specifically inhibited by antisense RNA," *J. Cell Biol.*, 101:1094–1099, 1985.

Herman et al., "Abnormal DNA methylation frequently inactivates the putative tumor suppressor DKDN2/p16 in many tumor types," *Proc Am Assoc Cancer Res*, 36:20, 1995.

Hermonat and Muzycska, "Use of adenoassociated virus as a mammalian DNA cloning vector: Transduction of neomycin resistance into mammalian tissue culture cells," *Proc. Nat. Acad. Sci. USA*, 81:6466–6470, 1984.

Hersdorffer et al., "Efficient gene transfer in live mice using a unique retroviral packaging line," *DNA Cell Biol.*, 9:713–723, 1990.

Herz and Gerard, "Adenovirus-mediated transfer of low density lipoprotein receptor gene acutely accelerates cholesterol clearance in normal mice," *Proc. Natl. Acad. Sci. USA* 90:2812–2816, 1993.

Horwich et al., "Synthesis of hepadnavirus particles that contain replication-defective duck hepatitis B virus genomes in cultured HuH7 cells," *J. Virol.*, 64:642–650, 1990.

Hussussian et al., "Germline p16 mutations in familial melanoma," *Nature Genetics*, 15–21, 1994.

Hynes, "Integrins: a family of cell surface receptors," *Cell*, 48:549–554, 1987.

Jones and Shenk, "Isolation of deletion and substitution mutants of adenovirus type 5," *Cell*, 13:181–188, 1978.

Kamb et al., "A cell cycle regulator potentially involved in genesis of many tumor types," *Science*, 2674:436–440, 1994.

Kamb et al., "Analysis of the p16 gene (CDKN2) as a candidate from chromosome 9P melanoma susceptibility locus," *Nature Genetics*, 8:22–26, 1994.

Kaneda et al., "Increased expression of DNA cointroduced with nuclear protein in adult rat liver," *Science*, 243:375–378, 1989.

Kato et al., "Expression of hepatitis B virus surface antigen in adult rat liver," *J. Biol. Chem.*, 266:3361–3364, 1991.

Klein et al., "High-velocity microprojectiles for delivering nucleic acids into living cells," *Nature*, 327:70–73, 1987.

Kyte and Doolittle, "A simple method for displaying the hydropathic character of a protein," *J. Mol. Biol.*, 157(1):105–132, 1982.

Le Gal La Salle et al., "An adenovirus vector for gene transfer into neurons and glia in the brain," *Science*, 259:988–990, 1993.

Levrero et al., "Defective and nondefective adenovirus vectors for expressing foreign genes in vitro and in vivo," *Gene*, 101: 195–202, 1991.

Li et al., "Assessment of recombinant adenoviral vectors for hepatic gene therapy," *Hum. Gene Ther.*, 4:403–409, 1993.

Mann et al., "Construction of a retrovirus packaging mutant and its use to produce helper-free defective retrovirus," *Cell*, 33:153–159, 1983.

Markowitz et al., "A safe packaging line for gene transfer: Separating viral genes on two different plasmids," *J. Virol.*, 62:1120–1124, 1988.

Marx, "Learning how to suppress cancer," *Science*, 261:1385–1387, 1993.

Mitsudomi et al., "p53 gene mutations in non-small-cell lung cancer cell lines and their correlation with the presence of ras mutations and clinical features," *Oncogene*, 7:171–180, 1992.

Mori et al., "Frequent somatic mutation of the MTS1/CDK4I (multiple tumor suppressor/cyclin-dependent kinase 4 inhibitor) gene in esophageal squamous cell carcinoma," *Cancer Res.*, 54:3396–3397, 1994.

Mulligan, "The basic science of gene therapy," *Science*, 260:9260–932, 1993.

Myers, EPO 0273085.

Neumaier et al., "Biliary glycoprotein, a potential human cell adhesion molecule, is down-regulated in colorectal carcinomas," *Proc. Natl. Acad. Sci. USA*, 90:10744–10748, 1993.

Nicolas and Rubenstein, "Retroviral vectors," In: Rodriguez R L, Denhardt D T, ed. Vectors: A survey of molecular cloning vectors and their uses. Stoneham: Butterworth, pp. 493–513, 1988.

Nicolau and Sene, "Liposome-mediated DNA transfer in eukaryotic cells," *Biochim. Biophys. Acta*, 721:185–190, 1982.

Nicolau et al., "Liposomes as carriers for in vivo gene transfer and expression," *Methods Enzymol.*, 149:157–176, 1987.

Nobri et al., "Deletions of the cyclin-dependent kinase-4 inhibitory gene in multiple human cancers," *Nature* (London), 368:753–756, 1995.

Okamoto et al., "Mutations and altered expression of p16$^{(INK4)}$ in human cancer," *Proc. Natl. Acad. Sci. USA*, 91:11045–11049, 1994.

Okamoto et al., "Mutations in the p16$^{(INK4)}$/MTS1/CDKN2, p15$^{(INK4B)}$/MTS2, and p18 genes in primary and metastatic lung cancer," *Cancer Res.*, 55:1448–1451, 1995.

Orlow et al., "Chromosome 9 allelic losses and microsatellite alterations in human bladder tumors," *Cancer Res.*, 54:2848–2851, 1994.

Paskind et al., "Dependence of moloney murine leukemia virus production on cell growth," *Virology*, 67:242–248, 1975.

Potter et al., "Enhancer-dependent expression of human k immunoglobulin genes introduced into mouse pre-B lymphocytes by electroporation," *Proc. Nat. Acad. Sci. USA*, 81:7161–7165, 1984.

Ragot et al., "Efficient adenovirus-mediated transfer of a human minidystrophin gene to skeletal muscle of mdx mice," *Nature*, 361:647–650, 1993.

Renan, "Cancer genes: current status, future prospects, and applicants in radiotherapy/oncology," *Radiother. Oncol.*, 19:197–218, 1990.

Rich et al., "Development and analysis of recombinant adenoviruses for gene therapy of cystic fibrosis," *Hum. Gene Ther.*, 4:461476, 1993.

Ridgeway, "Mammalian expression vectors," In: Rodriguez R L, Denhardt D T, ed. Vectors: A survey of molecular cloning vectors and their uses. Stoneham: Butterworth, pp. 467–492, 1988.

Rippe et al., "DNA-mediated gene transfer into adult rat hepatocytes in primary culture," *Mol. Cell Biol.*, 10:689–695, 1990.

Rosenfeld et al., "Adenovirus-mediated transfer of a recombinant α1-antitrypsin gene to the lung epithelium in vivo," *Science*, 252:431–434, 1991.

Rosenfeld et al., "In vivo transfer of the human cystic fibrosis transmembrane conductance regulator gene to the airway epithelium," *Cell*, 68:143–155, 1992.

Roux et al., "A versatile and potentially general approach to the targeting of specific cell types by retroviruses: Application to the infection of human cells by means of major histocompatibility complex class I and class II antigens by mouse ecotropic murine leukemia virus-derived viruses," *Proc. Natl. Acad. Sci. USA*, 86:9079–9083, 1989.

Rubinfeld et al., "Association of the APC gene product with β-catenin," *Science*, 262:1731–1734, 1993.

Serrano et al., "A new regulatory motif in cell-cycle control causing specific inhibition of cyclin D/CDK4," *Nature*, 366:704–707, 1993.

Serrano et al., "Inhibition of ras-induced proliferation and cellular transformation by pf16$^{INK14}$," *Science*, 267:249–252, 1995.

Southern and Berg, "Transformation of Mammalian Cells to Antibiotic Resistance with a Bacterial Gene Under Control of the SV40 Early Region Promoter," *Journal of Molecular and Applied Genetics*, 1:327–341, 1982.

Stratford-Perricaudet and Perricaudet, "Gene transfer into animals: the promise of adenovirus," p. 51–61, In: *Human Gene Transfer*, Eds, O. Cohen-Haguenauer and M. Boiron, Editions John Libbey Eurotext, France, 1991.

Stratford-Perricaudet et al., "Evaluation of the transfer and expression in mice of an enzyme-encoding gene using a human adenovirus vector," *Hum. Gene Ther.*, 1:241–256, 1990.

Takahashi et al., "p53: a frequent target for genetic abnormalities in lung cancer," *Science*, 246:491–494, 1989.

Temin, "Retrovirus vectors for gene transfer: Efficient integration into and expression of exogenous DNA in vertebrate cell genome," In: Kucherlapati R, ed. Gene transfer. New York: Plenum Press, pp. 149–188, 1986.

Top et al., "Immunization with live types 7 and 4 adenovirus vaccines. II. Antibody response and protective effect against acute respiratory disease due to adenovirus type 7," *J. Infect. Dis.*, 124:155–160, 1971.

Trofatter et al., "A novel moesin-, ezrin-, radixin-like gene is a candidate for the neurofibromatosis 2 tumor suppressor," *Cell*, 72:791–800, 1993.

Tur-Kaspa et al., "Use of electroporation to introduce biologically active foreign genes into primary rat hepatocytes," *Mol. Cell Biol.*, 6:716–718, 1986.

Varmus et al., "Retroviruses as mutagens: Insertion and excision of a nontransforming provirus alter the expression of a resident transforming provirus," *Cell*, 25:23–36, 1981.

Wagner et al., *Science*, 260:1510–1513, 1993.

Warner and Heston, "Future developments of nonhormonal systemic therapy for prostatic carcinoma," *Urol. Clin. N. Am.*, 18:25–33, 1991.

Wong et al., "Appearance of β-lactamase activity in animal cells upon liposome mediated gene transfer," *Gene*, 10:87–94, 1980.

Wu and Wu, "Evidence for targeted gene delivery to HepG2 hepatoma cells in vitro," *Biochemistry*, 27:887–892, 1988.

Wu and Wu, "Receptor-mediated in vitro gene transfections by a soluble DNA carrier system," *J. Biol. Chem.*, 262:4429–4432, 1987.

Yang et al., "In vivo and in vitro gene transfer to mammalian somatic cells by particle bombardment," *Proc. Natl. Acad. Sci. USA*, 87:9568–9572, 1990.

Zelenin et al., "High-velocity mechanical DNA transfer of the chloramphenicol acetyltransferase gene into rodent liver, kidney and mammary gland cells in organ explants and in vivo," *FEBS Lett.*, 280:94–96, 1991.

Zhang et al., "Generation and identification of recombinant adenovirus by liposome-mediated transfection and PCR analysis," *Biotechniques*, 15:868–872, 1993.

Zhang et al., "High-efficiency gene transfer and high-level expression of wild-type p53 in human lung cancer cells mediated by recombinant adenovirus," *Cancer Gene Therapy*, 1:5–13, 1994.

Zhou et al., "The MTS1 gene is frequently mutated in primary human esophageal tumors," *Oncogene*, 9:3737–3741, 1994.

What is claimed is:

1. A method of inhibiting tumor growth in a mammal comprising:
   (i) providing a pharmaceutical composition comprising (a) an adenoviral vector comprising a promoter functional in eukaryotic cells and a nucleic acid encoding a p16, said nucleic acid being under the control of said promoter and positioned in a sense orientation to said promoter, and (b) a pharmaceutically acceptable buffer, solvent or diluent; and
   (ii) administering said pharmaceutical composition to said mammal by direct intratumoral administration.

2. The method according to claim 1, wherein said mammal is a human.

3. The method according to claim 1, wherein said tumor is a lung cancer tumor, a bladder cancer tumor, an esophageal cancer tumor, a pancreatic cancer tumor, a head and neck cancer tumor, a glioma, or a melanoma.

4. The method according to claim 1, wherein said adenoviral vector further comprises a polyadenylation signal 3' to said p16 encoding nucleic acid.

5. The method according to claim 1, wherein said adenoviral vector is a replication deficient adenovirus.

6. The method according to claim 5, wherein said adenoviral vector lacks at least a portion of the E1 region.

7. The method according to claim 6, wherein said adenoviral vector lacks the entire E1 region.

8. The method according to claim 1, wherein said direct intratumoral administration comprises three doses of adenoviral vector totalling $10^{10}$ PFU.

9. The method according to claim 1, wherein said promoter is selected from the group consisting of CMV IE, SV40 early, RSV LTR, tyrosinase, alpha-fetoprotein, albumin, PSA and PAI-1.

10. The method according to claim 1, wherein said promoter is CMV IE.

11. The method according to claim 1, wherein said nucleic acid encoding p16 is a cDNA.

12. The method according to claim 1, wherein said pharmaceutical composition comprises adenoviral vector at $10^9$ to $10^{11}$ PFU/ml.

13. The method according to claim 1, wherein said administration comprises injection.

* * * * *

UNITED STATES PATENT AND TRADEMARK OFFICE
CERTIFICATE OF CORRECTION

| | |
|---|---|
| PATENT NO. | : 6,251,871 B1 |
| APPLICATION NO. | : 08/910722 |
| DATED | : June 26, 2001 |
| INVENTOR(S) | : Xiaomei Jin and Jack A. Roth |

It is certified that error appears in the above-identified patent and that said Letters Patent is hereby corrected as shown below:

Page 1, Line 7 delete "The government may own certain rights in the present invention pursuant to grant number CA 45187 from the National Institutes of Health and Core Grant CA 16672." and insert -- This invention was made with government support under Grant Nos. CA 45187 and Core Grant CA 16672 awarded by National Institute of Health. The government has certain rights in the invention. --

Signed and Sealed this

Twenty-third Day of October, 2007

JON W. DUDAS
*Director of the United States Patent and Trademark Office*

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
        (A) LENGTH: 987 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:1:

```
CGGAGAGGGG GAGAACAGAC AACGGGCGGC GGGGAGCAGC ATGGAGCCGG CGGCGGGGAG    60

CAGCATGGAG CCTTCGGCTG ACTGGCTGGC CACGGCCGCG GCCCGGGGTC GGGTAGAGGA   120

GGTGCGGGCG CTGCTGGAGG CGGGGGCGCT GCCCAACGCA CCGAATAGTT ACGGTCGGAG   180

GCCGATCCAG GTCATGATGA TGGGCAGCGC CCGAGTGGCG GAGCTGCTGC TGCTCCACGG   240

CGCGGAGCCC AACTGCGCCG ACCCCGCCAC TCTCACCCGA CCCGTGCACG ACGCTGCCCG   300

GGAGGGCTTC CTGGACACGC TGGTGGTGCT GCACCGGGCC GGGGCGCGGC TGGACGTGCG   360

CGATGCCTGG GGCCGTCTGC CCGTGGACCT GGCTGAGGAG CTGGGCCATC GCGATGTCGC   420

ACGGTACCTG CGCGCGGCTG CGGGGGGCAC CAGAGGCAGT AACCATGCCC GCATAGATGC   480

CGCGGAAGGT CCCTCAGACA TCCCCGATTG AAAGAACCAG AGAGGCTCTG AGAAACCTCG   540

GGAAACTTAG ATCATCAGTC ACCGAAGGTC CTACAGGGCC ACAACTGCCC CCGCCACAAC   600

CCACCCCGCT TTCGTAGTTT TCATTTAGAA AATAGAGCTT TTAAAAATGT CCTGCCTTTT   660

AACGTAGATA TAAGCCTTCC CCCACTACCG TAAATGTCCA TTTATATCAT TTTTTATATA   720

TTCTTATAAA AATGTAAAAA AGAAAAACAC CGCTTCTGCC TTTTCACTGT GTTGGAGTTT   780

TCTGGAGTGA GCACTCACGC CCTAAGCGCA CATTCATGTG GGCATTTCTT GCGAGCCTCG   840

CAGCCTCCGG AAGCTGTCGA CTTCATGACA AGCATTTTGT GAACTAGGGA AGCTCAGGGG   900

GGTTACTGGC TTCTCTTGAG TCACACTGCT AGCAAATGGC AGAACCAAAG CTCAAATAAA   960

AATAAAATAA TTTTCATTCA TTCACTC                                       987
```

(2) INFORMATION FOR SEQ ID NO:2:

(i) SEQUENCE CHARACTERISTICS:
        (A) LENGTH: 156 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Glu Pro Ala Ala Gly Ser Ser Met Glu Pro Ser Ala Asp Trp Leu
 1               5                  10                  15

Ala Thr Ala Ala Ala Arg Gly Arg Val Glu Glu Val Arg Ala Leu Leu
                20                  25                  30

Glu Ala Gly Ala Leu Pro Asn Ala Pro Asn Ser Tyr Gly Arg Arg Pro
            35                  40                  45

Ile Gln Val Met Met Met Gly Ser Ala Arg Val Ala Glu Leu Leu Leu
        50                  55                  60
```

Leu His Gly Ala Glu Pro Asn Cys Ala Asp Pro Ala Thr Leu Thr Arg
65                  70                  75                  80

Pro Val His Asp Ala Ala Arg Glu Gly Phe Leu Asp Thr Leu Val Val
                85                  90                  95

Leu His Arg Ala Gly Ala Arg Leu Asp Val Arg Asp Ala Trp Gly Arg
            100                 105                 110

Leu Pro Val Asp Leu Ala Glu Glu Leu Gly His Arg Asp Val Ala Arg
        115                 120                 125

Tyr Leu Arg Ala Ala Gly Gly Thr Arg Gly Ser Asn His Ala Arg
    130                 135                 140

Ile Asp Ala Ala Glu Gly Pro Ser Asp Ile Pro Asp
145                 150                 155

(2) INFORMATION FOR SEQ ID NO:3:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:3:

ATGGAGCCTT CGGCTGACTG G                                        21

(2) INFORMATION FOR SEQ ID NO:4:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:4:

CCTGTAGGAC CTTCGGTGAC T                                        21

(2) INFORMATION FOR SEQ ID NO:5:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:5:

GATCCGGCGG CGGGGAGCAG CATGGAGCCT TCGGCTGACT GG                  42

(2) INFORMATION FOR SEQ ID NO:6:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

```
    (xi) SEQUENCE DESCRIPTION: SEQ ID NO:6:

GCCTCTCTGG TTCTTTCA                                                    18

(2) INFORMATION FOR SEQ ID NO:7:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:7:

CGGGCGGGGA GCAGCATGGA GCCGGCGGCG GGGAGC                                36
```